US012642827B2

(12) United States Patent
Boukherroub et al.

(10) Patent No.: US 12,642,827 B2
(45) Date of Patent: Jun. 2, 2026

(54) LACTIC ACID BACTERIA STRAIN—ANTIBACTERIAL PEPTIDES PRODUCED BY SAID STRAIN AND RELATED PHARMACEUTICAL COMPOSITIONS

(71) Applicants: UNIVERSITE DE LILLE, Lille (FR); CENTRE NATIONAL DE LA RECHERCHE SCIENTIFIQUE, Paris (FR); YNCREA HAUTS DE FRANCE, Lille (FR); UNIVERSITE DU LITTORAL CÔTE D'OPALE, Dunkirk (FR); UNIVERSITE D'ARTOIS, Arras (FR); UNIVERSITE POLYTECHNIQUE DES HAUTS DE FRANCE, Valenciennes (FR); CENTRALE LILLE INSTITUT, Villeneuve d'Ascq (FR)

(72) Inventors: Rabah Boukherroub, Villeneuve d'Ascq (FR); Djamel Drider, Roubaix (FR); Noura Hazime, Villeneuve d'Ascq (FR); Yanath Belguesmia, Lille (FR); Kamel Bendjeddou, Bejaia (DZ)

(73) Assignee: ADD2LIFE GMBH, Wiener Neustadt (AT)

( * ) Notice: Subject to any disclaimer, the term of this patent is extended or adjusted under 35 U.S.C. 154(b) by 932 days.

(21) Appl. No.: 17/616,156

(22) PCT Filed: Jun. 3, 2020

(86) PCT No.: PCT/EP2020/065376
§ 371 (c)(1),
(2) Date: Dec. 2, 2021

(87) PCT Pub. No.: WO2020/245216
PCT Pub. Date: Dec. 10, 2020

(65) Prior Publication Data
US 2022/0249583 A1      Aug. 11, 2022

(30) Foreign Application Priority Data
Jun. 7, 2019 (EP) .................................... 19178926

(51) Int. Cl.
| | |
|---|---|
| *A61K 35/747* | (2015.01) |
| *A61K 36/02* | (2006.01) |
| *A61K 38/16* | (2006.01) |
| *A61K 45/06* | (2006.01) |
| *A61P 31/00* | (2006.01) |

(52) U.S. Cl.
CPC ............ *A61K 35/747* (2013.01); *A61K 36/02* (2013.01); *A61K 38/164* (2013.01); *A61K 45/06* (2013.01); *A61P 31/00* (2018.01)

(58) Field of Classification Search
CPC ...... A61K 35/747; A61K 36/02; A61K 38/00; A61K 38/164; A61K 45/06; A61P 31/00; C07K 14/335; C12N 1/205; C12R 2001/225
See application file for complete search history.

(56) References Cited

U.S. PATENT DOCUMENTS 8,470,583 B1      6/2013   Liu et al.

OTHER PUBLICATIONS

Zohri et al. "A Comparative Study Between the Antibacterial Effect of Nisin and Nisin-Loaded Chitosan/Alginate Nanoparticles on the Growth of *Staphylococcus aureus* in Raw and Pasteurized Milk Samples", Probiotics & Antimicrobial Proteins, 2010, vol. 2, pp. 258-266. (Year: 2010).*
GenBank reference corresponding to accession No. AKU60537.1, deposited in GenBank on Aug. 5, 2015 (Year: 2015).*
Algburi et al. "Control of Biofilm Formation: Antibiotics and Beyond", Applied and Environmental Microbiology, 2017, vol. 83, article e02508-16, 15 pages. (Year: 2017).*
Lozo et al. "Characterization and Antimicrobial Activity of Bacteriocin 217 Produced by Natural Isolate *Lactobacillus paracasei* subsp. *paracasei* BGBUK2-16", Journal of Food Protection, 2004, vol. 67, No. 12, pp. 2727-2734. (Year: 2004).*
Chu et al. "Nanoparticle drug loading as a design parameter to improve docetaxel pharmacokinetics and efficacy", Biomaterials, 2013, vol. 34, Issue 33, pp. 8424-8429. (Year: 2013).*
GenBank reference corresponding to accession No. WP_032675994, deposited in GenBank on Mar. 18, 2024 (Year: 2024).*
Shin et al. "Biomedical Applications of Nisin", Journal of Applied Microbiology, 2016, vol. 120, Issue 6, pp. 1449-1465. (Year: 2016).*
Śliżewska et al. "Growth Kinetics of Probiotic Lactobacillus Strains in the Alternative, Cost-Efficient Semi-Solid Fermentation Medium", Biology, 2020, vol. 9, No. 12, article 423, 13 pages. (Year: 2020).*
Abedi et al. "Lactic acid production—producing microorganisms and substrate sources—state of art", Heliyon, 2020, vol. 6, article e04974, 32 pages. (Year: 2020).*
Parada et al. "Bacteriocins from lactic acid bacteria: purification, properties and use as biopreservatives", Brazilian Archives of Biology and Technology, 2007, vol. 50, No. 3, pp. 521-542. (Year: 2007).*

(Continued)

*Primary Examiner* — Louise W Humphrey
*Assistant Examiner* — Deepa Mishra
(74) *Attorney, Agent, or Firm* — H&I PARTNERS; Chai Im; C. Andrew Im

(57) ABSTRACT

A *Lactobacillus paracasei* strain deposited at the CNCM under reference number CNCM I-5369. A mixture of the peptides having the following sequences: (SEQ ID NO 1), (SEQ ID NO 2), (SEQ ID NO 3), (SEQ ID NO 4) and (SEQ ID NO 5) and to one of the above-mentioned peptides in combination with at least one component chosen among: essential oils and particularly among essential oil of mint, essential oil of thyme, essential oil of pine tree, menthol, thymol, pinene, vitamin C, formic acid, propionic acid, citric acid, sorbic acid and lactic acid and/or a nanoparticle which may be loaded with said active ingredients.

9 Claims, 9 Drawing Sheets

Specification includes a Sequence Listing.

(56)          References Cited

OTHER PUBLICATIONS

Jingping GE et al., "Purification and Partial Characterization of a Novel Bacteriocin Synthesized by Lactobacillus paracasei HD1-7 Isolated from Chinese Sauerkraut Juice," Scientific Reports, Jan. 14, 2016, pp. 1-7, vol. 6, No. 1.

D. Hernandez et al., "Antimicrobial activity of lactic acid bacteria isolated from Tenerife cheese: initial characterization of plantaricin TF711, a bacteriocin-like substance produced by Lactobacillus plantarum TF711," J. Applied Microbiology, Jul. 1, 2005, pp. 77-84, vol. 99, No. 1.

B. Batdorj et al., "Purification and characterization of two bacteriocins produced by lactic acid bacteria isolated from Mongolian airag," J. Applied Microbiology, Oct. 1, 2006, vol. 101, No. 4.

Yanath Belguesmia et al., "Heterologous Biosynthesis of Five New Class II Bacteriocins From Lactobacillus paracasei CNCM I-5369 With Antagonistic Activity Against Pathogenic *Escherichia coli* Strains," Frontiers in Microbiology, Jun. 19, 2020, pp. 1-9, vol. 11.

Database UniProt [Online], "SubName: Full=Bacteriocin," Jan. 9, 2013, retrieved from EBI accession No. UNIPROT:K6RWW6, XP055716500.

Database UniProt [Online], "SubName: Full=ComC/BlpC family leader-containing pheromone/bacteriocin," Jun. 7, 2017, retrieved from EBI accession No. UNIPROT:A0A1VOQ9A4, XP055716503.

Database UniProt [Online], "SubName: Full=Uncharacterized protein," Oct. 16, 2013, retrieved from EBI accession No. UNIPROT:S4ZS63, XP055716506.

Database UniProt [Online], "SubName: Full=Bacteriocin immunity protein," May 8, 2019, retrieved from EBI accession No. UNIPROT:A0A454XR65, XP055716511.

Database UniProt [Online], "SubName: Full=Uncharacterized protein," Jun. 7, 2017, retrieved from EBI accession No. UNIPROT:S2PWS1, XP055716519.

Database Refseq [Online], "Multispecies: bacteriocin [Lactobacillus]," Apr. 17, 2017, retrieved from NCBI accession No. REFSEQ:WP_003567356, XP002794521.

Database UniProt [Online], "SubName: Full=Putative membrane protein," Sep. 18, 2013, retrieved from EBI accession No. UNIPROT:S2N8D7, XP002794522.

Database Refseq [Online], "Multispecies: ComC/Blpc family leader-containing pheromone/bacteriocin [Lactobacillus]," Apr. 9, 2019, retrieved from NCBI accession No. REFSEQ:WP_003567358, XP002794523.

Database UniProt [Online], "SubName: Full=Uncharacterized protein," Sep. 18, 2013, retrieved from EBI accession No. UNIPROT:S2RBY0, XP002794524.

Database UniProt [Online], "SubName: Full=Uncharacterized protein," Sep. 18, 2013, retrieved from EBI accession No. UNIPROT:S2RGS0, XP002794525.

Database Refseq [Online], "Multispecies: bacteriocin immunity protein [Lactobacillus casei group]," May 13, 2017, retrieved from NCBI accession No. REFSEQ:WP_003580886, XP002794526.

Database UniProt [Online], "SubName: Full=Prebacteriocin," May 8, 2019, retrieved from EBI accession No. UNIPROT:A0A454XR65, XP002794527.

Database EMBL [Online], "Lactobacillus paracasei hypothetical protein ID—AKU60549; SV 1; linear; genomic DNA; STD; Pro; 306 BP.," Aug. 24, 2015, retrieved from EBI accession No. EML:AKU60549, XP002794528.

Database EMBL [Online], "Lactobacillus paracasei predicted protein ID—BBF75321; SV 1; linear; genomic DNA; STD; Pro; 306 BP.," Jul. 30, 2018, retrieved from EBI accession No. EML:BBF75321, XP002794529.

Database UniProt [Online], "SubName: Full=Bacteriocin class II with double-glycine leader peptide," Jun. 7, 2017, retrieved from EBI accession No. UNIPROT:A0A1V0Q993, XP002794530.

* cited by examiner

SEQUENCE LISTING

```
<160> NUMBER OF SEQ ID NOS: 5

<210> SEQ ID NO 1
<211> LENGTH: 60
<212> TYPE: PRT
<213> ORGANISM: Lactobacillus paracasei

<400> SEQUENCE: 1

Met Tyr Thr Met Thr Asn Leu Lys Asp Lys Glu Leu Ser Gln Ile Thr
1               5                   10                  15

Gly Gly Phe Ala Phe Val Ile Pro Val Ala Ala Ile Leu Gly Phe Leu
            20                  25                  30

Ala Ser Asp Ala Trp Ser His Ala Asp Glu Ile Ala Gly Gly Ala Thr
        35                  40                  45

Ser Gly Trp Ser Leu Ala Asp Lys Ser His Ser Leu
    50                  55                  60

<210> SEQ ID NO 2
<211> LENGTH: 62
<212> TYPE: PRT
<213> ORGANISM: Lactobacillus paracasei

<400> SEQUENCE: 2

Met Gln Gln Phe Met Thr Leu Asp Asn Ser Ser Leu Glu Lys Ile Ala
1               5                   10                  15

Gly Gly Glu Asn Gly Gly Leu Trp Ser Ile Ile Gly Phe Gly Leu Gly
            20                  25                  30

Phe Ser Ala Arg Ser Val Leu Thr Gly Ser Leu Phe Val Pro Ser Arg
        35                  40                  45

Gly Pro Val Ile Asp Leu Val Lys Gln Leu Thr Pro Lys Asn
    50                  55                  60
```

-continued

```
<210> SEQ ID NO 3
<211> LENGTH: 29
<212> TYPE: PRT
<213> ORGANISM: Lactobacillus paracasei

<400> SEQUENCE: 3

Met Leu Ile Leu Gly Leu Ile Ala Ile Asp Ala Trp Ser His Thr Asp
1               5                   10                  15

Gln Ile Ile Ala Gly Phe Leu Lys Gly Trp Gln Gly Met
            20                  25

<210> SEQ ID NO 4
<211> LENGTH: 111
<212> TYPE: PRT
<213> ORGANISM: Lactobacillus paracasei

<400> SEQUENCE: 4

Met Thr Asp Lys Arg Glu Thr Leu Met Ser Met Leu Ser Lys Ala Tyr
1               5                   10                  15

Ala Asn Pro Thr Ile Lys Ala Glu Pro Ala Leu Arg Ala Leu Ile Glu
            20                  25                  30

Thr Asn Ala Lys Lys Val Asp Glu Gly Asp Asp Glu Lys Ala Tyr Val
        35                  40                  45

Thr Ala Val Thr Gln Leu Ser His Asp Ile Ser Lys Tyr Tyr Leu Ile
        50                  55                  60

His His Ala Val Pro Glu Glu Leu Val Ala Val Phe Asn Tyr Ile Lys
65                  70                  75                  80

Lys Asp Val Pro Ala Ala Asp Ile Asp Ala Ala Arg Tyr Arg Ala Gln
                85                  90                  95

Ala Leu Ala Ala Gly Leu Val Ala Ile Pro Ile Val Trp Gly His
            100                 105                 110

<210> SEQ ID NO 5
<211> LENGTH: 101
<212> TYPE: PRT
<213> ORGANISM: Lactobacillus paracasei

<400> SEQUENCE: 5

Met Tyr Val Lys Asp Ser Lys Val Asp Leu Thr Gln Asn Asn Leu Leu
1               5                   10                  15

Pro Phe Glu Glu Lys Arg Lys Ile Met Ser Tyr Asn Tyr Arg Gln Leu
            20                  25                  30

Asp Asp Phe Gln Leu Ser Gly Val Ser Gly Gly Lys Lys Lys Phe Asp
        35                  40                  45

Cys Ala Ala Thr Phe Val Thr Gly Ile Thr Ala Gly Ile Gly Ser Gly
        50                  55                  60

Thr Ile Thr Gly Leu Ala Gly Gly Pro Phe Gly Ile Ile Gly Gly Ala
65                  70                  75                  80

Val Val Gly Gly Asn Leu Gly Ala Val Gly Ser Ala Ile Lys Cys Leu
                85                  90                  95

Gly Asp Gly Met Gln
            100
```

LACTIC ACID BACTERIA STRAIN—ANTIBACTERIAL PEPTIDES PRODUCED BY SAID STRAIN AND RELATED PHARMACEUTICAL COMPOSITIONS

RELATED APPLICATIONS

This application is a § 371 application of PCT/EP2020/065376 filed Jun. 3, 2020, which claims priority from French Patent Application No. 19178926.2 filed Jun. 7, 2019, each of which is incorporated herein by reference in its entirety.

TECHNICAL FIELD

The present invention relates to a novel lactic acid bacterium strain and to 5 novel peptides having antibiotic/antimicrobial properties and more particularly having antimicrobial properties against *Escherichia coli* (*E. coli*) and even against colistin-resistant strains of *Escherichia coli* (*E. coli*).

BACKGROUND OF THE INVENTION

Resistance to antibiotics, designed as antimicrobial resistance (AMR) has become a well-acknowledged crisis in the world. Thus, alternatives to replace fading and aging antibiotics, are timely and absolutely needed. The antibiotics consumption in animal production is steadily growing in the world. Recently the WHO recommended the reasonable use of "least important" antibiotics to limit the development of so-called "critically important" resistance to antibiotics for human health. Moreover in the WHO report, edited in October 2017, the following recommendations were made for the agricultural sector in order to prevent and mitigate the spread of antibiotic resistance: antibiotics have to be administrated to animals only under veterinary control; antibiotics should not be used as growth promoters or to prevent disease in animals; vaccination of animals has to be implemented to reduce the need for antibiotics and to use alternatives to these drugs if they exist; promote and apply good practices at every stage of the production and processing of animal and plant foods; increase biosecurity on farms to avoid infections by improving animal hygiene and welfare.

Alternatives approaches currently considered include a better management of existing antibiotics, modification of their structure to improve their activities and the search for new antibiotic molecules such as antimicrobial peptides (AMPs), which are produced by all living organisms (Nes, I. F. (2011). History, Current Knowledge, and Future Directions on Bacteriocin Research of Lactic Acid Bacteria. In Prokaryotic Antimicrobial Peptides: From Genes to Application edited by Djamel Drider, Sylvie Rebuffat. Springer. NY: 3-12). AMPs produced by unicellular organisms (especially bacteria) include lipopeptides, which are non-ribosomally synthesized secondary metabolites, and bacteriocins that are ribosomally synthesized by Gram-negative and Gram-positive bacteria, and to a lesser extent by Archea. Bacteriocins produced by lactic acid bacteria (LAB-bacteriocins) are heat stable and active over a wide range of pH values. They are mainly active against strains that phylogenetically related to the bacteriocin producing strain. However, LAB-bacteriocins with activities against phylogenetically distant strains are scarce. Noteworthy, the discovery of new strains of LAB (Lactic Acid Bacteria) producing new bacteriocins with activity against Gram-negative bacilli (GNB) is original for academic achievements and insights, and important for industrial and biomedical applications.

The lack of therapeutic options to treat infections caused by multidrug-resistant GNB enabled to rehabilitate colistin as an antibiotic of last resort for need in the human medicine. However, this antibiotic has been largely used in the veterinary medicine to treat colibacillosis diarrhea, which is responsible consequently for significant economic losses. The use of colistin is a major issue for human medicine as for veterinary practices in breeding. Nevertheless, the identification of bacterial resistance to colistin, including the discovery of the first transferable mechanism of resistance to colistin (mcr-1, mcr-2, mcr-3, mcr-4 and then mcr-5) (see Borowiak, M., Fischer, J., Hammerl, J. A., Hendriksen, R. S., Szabo, I., Malorny, B. (2017). Then, the identification of a novel transposon-associated phosphoethanolamine transferase gene, mcr-5, conferring colistin resistance in d-tartrate fermenting *Salmonella enterica* subsp. *enterica* serovar Paratyphi B. J Antimicrobial Chemother. 2017 Dec. 1; 72(12):3317-3324. doi: 10.1093/jac/dkx327) has conducted European agencies to reassess the risk profile of colistin. With regard to that the European Center for Disease Prevention and Control (ECDC) has recently published a report suggesting limiting the use of colistin in the animal sector. In turn, ANSES, in its report of October 2016 (no 2016-SA-0160), recommended to bolster key alternatives to antibiotics, in particularly to colistin for the treatment and/or metaphylaxis in the animal sector.

U.S. Pat. No. 8,470,583 discloses a *Lactobacillus paracasei* strain deposited as NRRL B-50314 that secretes a bacteriocin. This bacteriocin has antibacterial activity against a range of Gram-positive bacteria, including but not limited to *Listeria monocytogenes, Staphylococcus aureus, Enterococcus faecalis* and other *Lactobacillus* species. Further, this bacteriocin has activity against methicillin resistant *Staphylococcus aureus*.

The development of antibiotic molecules to control emerging infections caused by GNB such as *Escherichia coli* (*E. coli*) is a subject of a big concern for both human and veterinary medicine.

OBJECT AND SUMMARY OF THE INVENTION

One purpose of the invention is to provide a new lactic acid bacterium strain able to produce five antibacterial/antimicrobial peptides, of proteinaceous nature meeting bacteriocins criteria.

Another purpose of the present invention is to provide a new bacterium strain able to prevent or limit bacterial adhesion, particularly, *E. coli* adhesion on eukaryotic cells, and particularly on human and/or pig intestinal cells.

One purpose of the present invention is to provide new antibacterial/antimicrobial compounds useful against GNB strains and particularly against *E. coli* strains.

Another purpose of the invention is to provide new compounds that can be used in combination with colistin to reduce the amount of colistin administrated or to potentiate the antibacterial activity of colistin.

Another purpose of the invention is to provide new antibacterial compounds efficient even against colistin-resistance strains and particularly of colistin-resistance *E. coli* strains.

Another purpose of the invention is to provide an active pharmaceutical composition and moreover a pharmaceutical having a non pH dependent activity.

Another purpose of the present invention is to provide a pharmaceutical composition or new antibacterial/antimicrobial compounds that have low probability of developing bacterial resistance.

Another purpose of the present invention is to provide antibacterial compounds which are not cytotoxic and particularly not cytotoxic for human and/or pig intestinal cells.

The present invention relates to the *Lactobacillus paracasei* ICVB411 strain deposited at the Collection Nationale De Culture de microorganisms (CNCM) under reference number CNCM I-5369 and its variants and mutants able to produce at least one peptide according to the claimed invention.

*Lactobacillus paracasei* ICVB411 strain is also called *Lactobacillus paracasei* CNCM I-5369 herein after.

*Lactobacillus paracasei* ICVB411 (*L. paracasei* CNCM I-5369) is able to produce five novel bacteriocins. These novel bacteriocins are synthesized and encountered in the culture supernatant. They were partially purified and successfully tested against a panel of *E. coli* strains, including *E. coli* carrying mcr-1 gene. The data provided here underlines the potential of LAB-bacteriocins as molecules potentially usable to treat colibacillosis infections in pigs and particularly in piglets. This invention will offer an opportunity to limit even eliminate antibiotics (and particularly colistin) from intensive breeding, and their replacement with bacteriocins produced by *L. paracasei* CNCM I-5369.

4

Figure 15A:
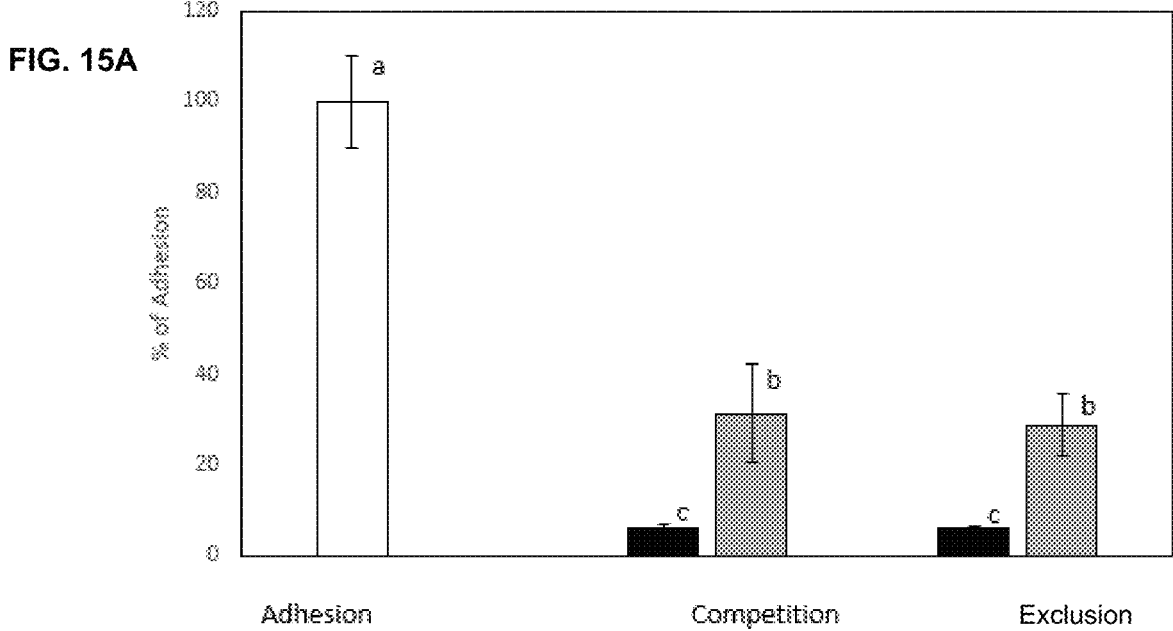
Figure 15B:
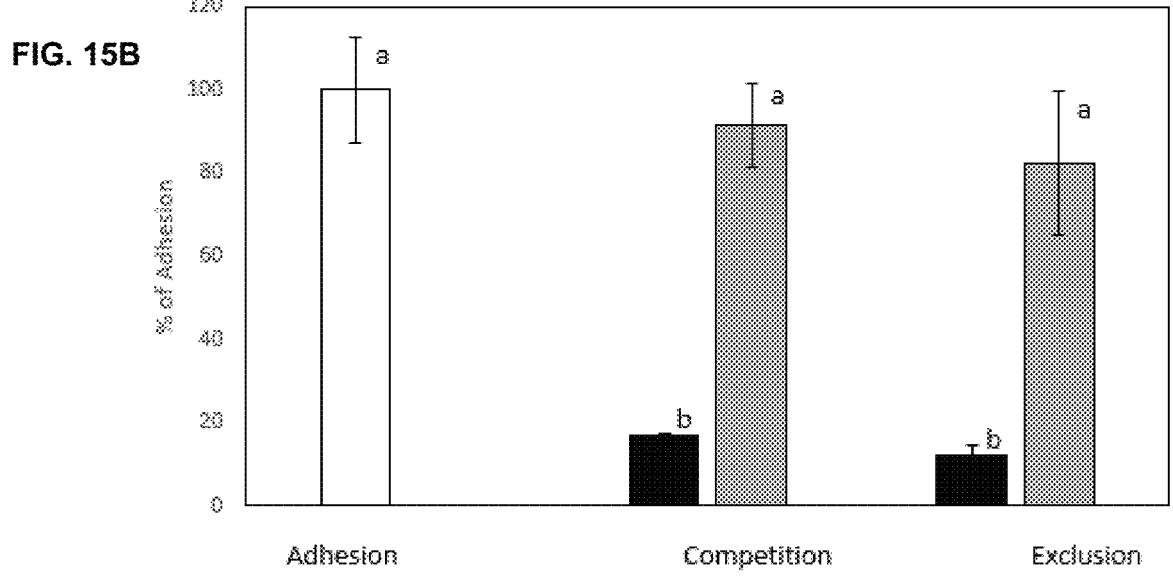

FIGS. 15A-B shows the percentages of adhesion of *E. coli* 184 strain to: Caco-2 monolayer cells in FIG. 15A; IPEC-1 monolayer cells in FIG. 15B; (white) alone, or during competition and exclusion assays in presence of (black) *Lactobacillus paracasei* CNCM I-5369 (bac+) strain, or in presence of (grey) of *Lactobacillus paracasei* FB1 (bac-) strain.

DETAILED DESCRIPTION OF EMBODIMENTS

The present invention also relates to an isolated peptide chosen among:

peptides having the following sequences:

```
                                        (SEQ ID NO 1)
MYTMTNLKDKELSQITGGFAFVIPVAAILGFLASDAWSHADEIAGGATS
GWSLADKSHSL;

(SEQ ID NO 2)
MQQFMTLDNSSLEKIAGGENGGLWSIIGFGLGFSARSVLTGSLFVPSRG
PVIDLVKQLTPKN;

(SEQ ID NO 3)
MLILGLIAIDAWSHTDQIIAGFLKGWQGM;

(SEQ ID NO 4)
MTDKRETLMSMLSKAYANPTIKAEPALRALIETNAKKVDEGDDEKAYVT
AVTQLSHDISKYYLIHHAVPEELVAVFNYIKKDVPAADIDAARYRAQAL
AAGLVAIPIVWGH;

(SEQ ID NO 5)
MYVKDSKVDLTQNNLLPFEEKRKIMSYNYRQLDDFQLSGVSGGKKKFDC
AATFVTGITAGIGSGTITGLAGGPFGIIGGAVVGGNLGAVGSAIKCLGD
GMQ
``` and among peptides having at least 90% and particularly at least 95% of identity with the above-mentioned sequences SEQ ID NO 1 to SEQ ID NO 5 and having an antibacterial activity and particularly an antibacterial activity on *E. coli* strains.

The antibacterial/antimicrobial mechanism of the peptides according to the invention is not known. However, most of peptides have an antibacterial/antimicrobial activity because they chemically react with the phospholipids of the bacteria/microbe external membrane. In other words, they destroy the microbe/bacteria external membrane. Since peptides interact chemically with the external membrane of the microbe/bacteria before entering thereinto, they do not involve microbe/bacteria resistance. Accordingly, the peptides of the invention and the pharmaceutical composition comprising said peptides have a low probability to develop bacteria/microbe resistance.

The present invention also relates to the isolated peptide as described above for its use as a medicament and particularly as an antibacterial or antimicrobial medicament and more particularly for its use in the treatment of *E. coli* infections and particularly colistin-resistant *E. coli* strains infections in a mammal in such need, said mammal being particularly chosen among pig, piglet, poultry, cattle, sheep, caprine animals and human.

Preferably, the invention relates to a mixture of the five above-mentioned peptides for its use as a medicament and particularly as an antibacterial or antimicrobial medicament and more particularly for its use in the treatment of *E. coli* infections and particularly colistin-resistant *E. coli* strains infections in a mammal in such need, said mammal being particularly chosen among pig, piglet, poultry, cattle, sheep, caprine animals and human.

The present invention also relates to a pharmaceutical composition comprising as an active ingredient, at least one peptide according to claimed invention and particularly the five peptides having the sequence SEQ ID NO 1 to SEQ ID NO 5 and/or the strain and a pharmaceutically acceptable excipient.

The pharmaceutically acceptable excipient may be chosen among purified water, ethyl alcohol, propylene glycol, glycerin, vegetal oils, lactose, sorbitol, starch, polymers or any other excipient described in the 7$^{th}$ edition of Handbook of Pharmaceutical Excipients (London Pharmaceutical Press 2012) and mixtures thereof.

Advantageously, the excipient is water or an aqueous solution.

Advantageously, the pharmaceutical composition comprises the five peptides above-mentioned and at least one excipient as above-mentioned.

According to one particular embodiment that can be combined with any one of the above-mentioned embodiments, the pharmaceutical composition comprises as an active ingredient, the supernatant of a culture of the strain according to claimed invention or consists in said supernatant, said supernatant being optionally purified. The supernatant can be purified by chromatography, for example and particularly can be purified on a reverse phase C18 and eluted with a water solution of acetonitrile containing 20% in volume of acetonitrile. The supernatant is preferably a cell-free supernatant. It can be obtained through culturing the strain of the claimed invention in a culture medium (MRS for example) at 37° C. during 24 to 30 h.

According to another embodiment that can be combined with any one of the above-mentioned embodiments, the pH of said pharmaceutical composition is equal or superior to 4 or equal or inferior to 5 and particularly equal to 4.5. The peptides of the invention are particularly efficient as antibacterial or antimicrobial and particularly against *E. coli* and colistin-resistant *E. coli* strains at a pH as above-mentioned.

According to another embodiment that can be combined with any one of the above-mentioned embodiments, the pharmaceutical composition of the invention further comprises, as an active ingredient, colistin and/or at least one component chosen among essential oils and particularly among essential oil of mint, essential oil of thyme, essential oil of pine tree, menthol, thymol, pinene, vitamin C, formic acid, citric acid, sorbic and lactic acid.

Each of the five peptides of the invention and the mixture of the five peptides of the invention have a synergetic antibacterial effect in combination with colistin. Using the peptide(s) of the invention with colistin (in mixture) enables to reduce the efficient dose of colistin. A mixture of colistin and at least one of the peptides of the invention and particularly the five peptides of the invention enables the reduction of the pharmaceutically active amount of said mixture, compared to the pharmaceutically active amount of peptide(s) of the invention when used alone, without colistin.

Essential oils and acids have also an antibacterial activity and can be used to improve the antibacterial or antimicrobial activity of the pharmaceutical composition as above-mentioned or to get a synergetic effect with at least one peptide of the invention, and preferably with the mixture of the five peptides of the invention or a mixture of colistin and at least one peptide of the invention and preferably the five peptides of the invention.

According to another embodiment that can be combined with any one of the above-mentioned embodiments, the pharmaceutical composition of the invention further comprises nanoparticles. Using nanoparticles can enable to reduce the amount of active(s) ingredient(s) of the pharmaceutical composition of the invention. Further, the inventors have shown that nanoparticles loaded with at least one peptide of the invention or advantageously with a mixture of the five peptides of the invention are efficient as antibacterial and in particular against *E. coli* strains (even colistin-resistant *E. coli* strains) whatever the pH of the pharmaceutical composition is. Moreover, nanoparticles and particularly sodium alginate nanoparticles can resist to digestion; accordingly, the pharmaceutical composition comprising such nanoparticles loaded with the at least one peptide of the invention and preferably with a mixture of the five peptides of the invention (the supernatant as above-mentioned, for instance) can be orally administrated.

This is also the case when a mixture of the five peptides of the invention (advantageously the supernatant of a culture of the strain according to the claimed invention) and a component as described above and/or colistin, particularly lactic acid and/or thymol and/or menthol is loaded on the nanoparticles and particularly on sodium alginate nanoparticles.

The nanoparticles are not limited according to the invention. According to one embodiment of the nanoparticles, they comprise at least alginate nanoparticles and particularly sodium alginate nanoparticles. Preferably, all the nanoparticles contained in the pharmaceutical are alginate nanoparticles and more particularly sodium alginate nanoparticles.

According to a particular embodiment of the nanoparticles, which can be combined with the above-mentioned embodiment, said nanoparticles have an average size equal or superior to 115 nm and equal to or inferior to 126 nm and particularly equal to 118 nm, 120 nm or 124 nm. These sizes of nanoparticles enable the nanoparticles loaded with the active ingredients to be particularly active as antibacterial or antimicrobial.

According to one embodiment, said nanoparticles are loaded with at least one of said five peptides according to the claimed invention and preferably with a mixture of said five peptides and particularly with the supernatant of a culture of the strain according to the claimed invention. According to a variant, the nanoparticles are loaded only with said peptide(s) as a pharmaceutically active ingredient. The loaded nanoparticles are pharmaceutically active ingredient.

According to another embodiment, said nanoparticles are loaded with a mixture comprising:

i) at least one of said five peptides according to claim, preferably with a mixture of said five peptides and particularly with the supernatant of a culture of the strain according to the claimed invention; and ii) colistin and/or iii) at least one component chosen among essential oils and particularly among essential oil of mint, essential oil of thyme, essential oil of pine tree, menthol, thymol, pinene, vitamin C, formic acid, propionic acid, citric acid, sorbic and lactic acid.

Nanoparticles loaded with a mixture of said five peptides (preferably the supernatant as described above) and a component as above described are efficient as antibacterial whatever the pH of the pharmaceutical composition is. This is particularly the case when a component as above-mentioned and/or colistin is also loaded in said nanoparticles. Further, theses loaded nanoparticles resist to digestion and thus can be administrated orally. These types of loaded nanoparticles are efficient as antimicrobial or antibacterial particularly against *E. coli* and even colistin resistant *E. coli* strains.

The pharmaceutical composition may further comprise nanoparticles loaded only with colistin and/or with a component chosen among essential oil of mint, essential oil of thyme, essential oil of pine tree, menthol, thymol, pinene, vitamin C, formic acid, propionic acid, citric acid, sorbic and lactic acid, as a pharmaceutically active compound. The nanoparticles which are not loaded with the peptides of the invention can further enhance the efficiency of the pharmaceutical composition of the invention.

The nanoparticles can also be loaded with the pharmaceutical composition according to the invention.

In all the afore-mentioned embodiment, the weight of the load of said nanoparticles is equal or inferior to 12.2% of the weight of said nanoparticles and particularly equal to 12%.

According to one particular embodiment, the pharmaceutical composition comprises 60 µg/mL of said at least one peptide and particularly 60 µg/mL of the mixture of the five peptides and particularly the supernatant as above-mentioned According to another embodiment which can be combined with the aforementioned embodiment, the pharmaceutical composition comprises a mixture of colistin and at least one peptide of the invention. This mixture comprises at least 80% (80% included) by weight of at least one peptide of the invention and particularly of the five peptides (preferably the supernatant) and 20% of colistin. According to a particular embodiment, the mixture of colistin and said peptide(s) comprises at least 99% and 99.2%, for example, of peptide(s) (preferably the supernatant) and 1% or less of colistin, preferably 0.8% of colistin.

According to another embodiment, the pharmaceutical composition contains 0.2-2% (0.2 and 2% included) by weight of said component with respect to said amount of peptide(s) and particularly, as regards lactic acid (1 µg/mL), menthol (10 µg/mL) or thymol (10 µg/mL). The preferred combinations are as follows: menthol 10 µg/mL combined with 50 µg/mL of the mixture of the five peptides (said supernatant); lactic acid 1 µg/mL with 60 µg/mL of the mixture of the five peptides (i.e.; said supernatant). These values give good results on *E. coli* strains.

According to another embodiment which can be combined with any one of the aforementioned embodiments, the pharmaceutical composition comprises nanoparticles loaded with 12% of their weight with a mixture of said five peptides (particularly said supernatant) or with a mixture of said five peptides and said component. According to another embodiment, nanoparticles are loaded with 12% by weight of a mixture of said supernatant and an amount equal to 0.1% or 0.2% of their weight of said component. Regarding lactic acid, the amount thereof can be 0.2% of the weight of the nanoparticles, for example. Regarding menthol and thymol, the amount of each thereof can be from 0.2%, to 6% by weight (0.2 and 6% included) and particularly 2% or 4%. A mixture of thymol and menthol can be used in an amount of 4% by weight to get good antibacterial results. The nanoparticles are preferably in all cases alginate nanoparticles and more preferably sodium alginate nanoparticles.

The amount of active ingredient in the pharmaceutical composition according to the invention depends on the mammal to be treated and to the strain to be killed. The Man skilled in the Art is able to determine the effective amount of the active ingredient contained in the pharmaceutical composition of the invention.

According to a particular embodiment which may have the characteristics above-mentioned, the invention relates to pharmaceutical composition comprising as active ingredients an isolated peptide chosen among peptides having the following sequences:

```
                                          (SEQ ID NO 1)
MYTMTNLKDKELSQITGGFAFVIPVAAILGFLASDAWSHADEIAGGATS
GWSLADKSHSL;

(SEQ ID NO 2)
MQQFMTLDNSSLEKIAGGENGGLWSIIGFGLGFSARSVLTGSLFVPSRG
PVIDLVKQLTPKN;

(SEQ ID NO 3)
MLILGLIAIDAWSHTDQIIAGFLKGWQGM;

(SEQ ID NO 4)
MTDKRETLMSMLSKAYANPTIKAEPALRALIETNAKKVDEGDDEKAYVT
AVTQLSHDISKYYLIHHAVPEELVAVFNYIKKDVPAADIDAARYRAQAL
AAGLVAIPIVWGH;

(SEQ ID NO 5)
MYVKDSKVDLTQNNLLPFEEKRKIMSYNYRQLDDFQLSGVSGGKKKFDC
AATFVTGITAGIGSGTITGLAGGPFGIIGGAVVGGNLGAVGSAIKCLGD
GMQ
``` and at least one component chosen among:

> essential oils and particularly among essential oil of mint, essential oil of thyme, essential oil of pine tree, menthol, thymol, pinene,
> vitamin C, formic acid, propionic acid, citric acid, sorbic acid and lactic acid; and/or
> a nanoparticle which may be loaded with said active ingredients.

According to this particular embodiment, the nanoparticles may comprise at least alginate nanoparticles and particularly sodium alginate nanoparticles or in that said nanoparticles consist in sodium alginate nanoparticles.

According to that embodiment, said nanoparticles have an average size equal or superior to 115 nm and equal to or inferior to 126 nm and particularly equal to 118 nm, 120 nm or 124 nm.

Further, according to this embodiment, the weight of the load of said nanoparticles is equal or inferior to 12.2% of the weight of said nanoparticles and particularly equal to 12%.

The present invention also relates to the *L. paracasei* ICVB411 deposited at the CNCM under reference number CNCM I-5369 for its use as a medicament.

The present invention also relates to *L. paracasei* ICVB411 deposited at the CNCM under reference number CNCM I-5369 for its use as an antioxidant agent in the treatment of a patient suffering from a disease chosen among acute and chronic pathological conditions, such as cardiovascular diseases, acute and chronic kidney diseases, neurodegenerative diseases, macular degeneration, chronic obstructive pulmonary disease, biliary diseases, diabetes, cancers and aging.

The present invention also relates to *L. paracasei* ICVB411 deposited at the CNCM under reference number CNCM I-5369 for its use in the treatment of hypercholesterolemia, particularly in the prevention of diseases such as stroke, high blood pressure, atherosclerosis, cardiovascular diseases, xanthomas, cancers, obesity, diabetes, neurodegenerative diseases, non-alcoholic fatty liver diseases.

The present invention also relates to the use of *L. paracasei* ICVB411 deposited at the CNCM under reference number CNCM I-5369 as an antioxidant. The present invention also relates to a preservative containing or consisting in *L. paracasei* ICVB411 deposited at the CNCM under reference number CNCM I-5369. The preservative may be a food preservative, a cosmetic preservative, a drug preservative, or a paint preservative, for example.

The present invention also relates to a product, particularly a liquid product containing *L. paracasei* ICVB411 deposited at the CNCM under reference number CNCM I-5369. The product may be a food product, a beverage, a drug, a cosmetic, wood, a biological sample, or a paint, for example.

The pharmaceutical composition can be a solution, a gel, a powder, a tablet or a capsule. It is preferably formulated to be orally administrated. However, it can be also formulated for a mucosal (sublingual or via inhalation, for instance), a topic, intradermic, intravenous or intramuscular administration.

Definitions

The terms "colistin-resistant *E. coli* strains" refer to *E. coli* strains with a minimal inhibitory concentration (MIC) >2 μg/mL and/or carrying gene involved in colistin resistance and particularly to strains carrying the mrc-1 gene.

The term "treatment" refers to prophylactic and curative treatment.

The term antibacterial is particularly related to antibacterial activity against GNB strains.

The term "nanoparticles loaded with" or "X loaded in nanoparticles" refer to nanoparticles comprising a compound, or a mixture of compounds adsorbed on their external surface. However, the compound or mixture can also be adsorbed on the internal surface of the nanoparticles when said nanoparticles are porous, for example.

The term "mixture of the peptides of the invention" preferably refers to the supernatant as described above and more preferably to the purified supernatant (E20 also referred as E20 fraction).

The terms "% of identity" relates to the percentage of amino acid residues which are identic in a sequence to be compared with respect of a reference sequence. The sequence to be compared may comprise deletion, substitution and/or insertion with respect to the reference sequence.

Experimental Results

1. Isolation and Purification of Lactic Acid Bacteria from Alatig Cheese

The strain *L. paracasei* ICVB411 (deposited at the CNCM under reference number CNCM I-5369) was isolated from a traditional Algerian dairy product, named Alatig cheese. This strain has, in first instance, displayed antagonism against *E. coli* strains through production of inhibitory compound(s) of proteinaceous nature. This/these inhibitory compound(s) was/were encountered in the culture supernatant obtained by centrifugation (8,000 g, 4° C., 10 min) following the growth of *L. paracasei* CNCM I-5369 on MRS medium (de Man et al. 1960). Nonetheless, this anti-*E. coli* activity was only observed at low pH values, comprised between 4 and 5.

10 g of the artisanal cheese "Alatig" were dissolved and homogenized in 90 mL of a sterile physiological saline sterile water. Then, a drop was taken from this diluted cheese and was surface seeded on MRS agar (Liofilchem, Italy) then incubated for 48 h at 30° C. This step was performed twice. The first using MRS agar (Liofilchem, Italy) adjusted to pH 6.5 and the second using MRS agar adjusted to pH 5.4 with 0.1 M HCl.

The purification of the isolated strains was done with the successive subcultures of colonies on MRS agar. Incubation was performed at 30° C. for 48 h. The purity of these strains was confirmed by the presence on agar of homogeneous colonies with identical morphologies including same appearance, same color, same size and same shape. Gram staining was used to confirm the purity of the isolated strains. Gram-positive bacteria without catalase activity were presumed to be LAB. They were stored at 4° C. in MRS broth (Biokar, France).

2. Antibacterial Activity of Isolated Strains

The antibacterial activity of the strains isolated from Alatig cheese was tested against different target organisms among, which *E. coli*. Thus, 9 mL of MRS broth were seeded with 1 mL of a fresh culture of 18 h of the target strain and incubated at 37° C. for 18 h. Then, 250 mL MRS broth were inoculated with 2% of this pre-culture containing $10^8$ CFU/mL, and incubated at 37° C. for 18 h. Cells were removed by centrifugation (12 000 g, 30 min, 4° C.). The resulting supernatant was sterilized by filtration through 0.22 μm of nitrocellulose membranes (Millipore Corp., Bedford, Mass., USA).

The antibacterial activity of the crude supernatant was tested on Muller Hinton agar (Merck) by the well diffusion method (Batdorj, B., Dalgalarrondo, M., Choiset, Y., Pedroche, J., Métro, F., Prévost, H., Chobert, J. M., Haertlé, T. (2006). "Purification and characterization of two bacteriocins produced by lactic acid bacteria isolated from Mongolian airag" Journal of Applied Chemistry https://doi.org/ 10.1111/j.1365-2672.2006.02966.x). Thus, a Petri-plate was inoculated at $10^7$ CFU/mL with a 24 h culture of the target strain (*E. coli* or *S. aureus*). The Petri dish was dried at room temperature for 15 min. Then, wells of 6 mm diameter and 4 mm deep were made in the agar. Next, 100 μL of the crude supernatant at native pH (pH 4.5) and at neutral pH (neutralized to pH 7.0 with a 1M NaOH solution) were deposited in the wells. Aliquots of 100 μL of MRS medium adjusted to the same pH values and sterilized by filtration were used as a negative control. The dish was pre-incubated for 2 h at 4° C. to stop the growth of the target strain and allow the diffusion of the inhibiting agents in the agar, it was then incubated for 24 h at 37° C. After this period of incubation, the antibacterial activity was evaluated by measuring the diameter of the zone inhibition around the wells.

At native pH, all tested strains were endowed with antibacterial activity against *E. coli* and *S. aureus* strains, exhibiting inhibition zones of different diameters. The upmost inhibition zone recorded was of about 17 mm diameter halo, and the strain responsible of this activity was selected and further characterized.

Importantly, no antibacterial activity was detected when the supernatant was neutralized, showing a possible role of organic acids in this antagonism. With respect to that, different studies have reported the inhibitory potential of lactobacilli through inhibitory compound(s) other than organic acids, most often of proteinaceous nature, and which stability was observed from pH 2 to pH 6 (Drider, D., Rebuffat, S. (2011). "Prokaryotic Antimicrobial Peptides: From Genes to Application" Editor. Springer. NY 451 pp)). Other studies suggested that LAB (Lactic acid bacteria) are able to produce inhibitory compounds, of proteinaceous nature, and fully active at acidic pH and partly active at neutral pH (Mortvedt-Abildgaa, C., Nissen-Meyer, J., Jelle, B., Grenov, B., Skaugen, M., Nes, I. F. (1995). "Production and pH-Dependent Bactericidal Activity of Lactocin S, a Lantibiotic from *Lactobacillus sake* L45"; Houlihan AJ1, Mantovani H C, Russell J B. (2004). "Effect of pH on the activity of bovicin HC5, a bacteriocin from *Streptococcus bovis* HC5" FEMS Microbiol Lett. 2004). The loss of antibacterial activity of the supernatant at a neutral pH does not exclude the presence of other active substances than organic acids, and active at an acidic pH. This hypothesis was confirmed by testing the MRS medium adjusted to a same pH value as the supernatant (pH 4.5) with 5M HCl. Indeed, no antibacterial activity was registered against *E. coli*.

3. Phenotypical Identification of the Upmost Antagonistic LAB Strain

The most active strains were identified with the API® 50 CHL gallery (bioMérieux, Marcy l'Etoile, France) using the manufacturer's recommendations. A bacterial suspension from several identical colonies of the producing strain after 24 h culture at 37° C. on MRS agar, was prepared and diluted in "API 50 CHL medium" until to reach an absorbance of 0.45 (opacity equal to 2 McFarland) at $600_{nm}$. After homogenization, the inoculated API 50 CHL medium was distributed in tubules of the gallery. Cups were covered with sterile paraffin oil, when necessary, to avoid a possible release of gas. The gallery was incubated at 37° C. for 48 h. After incubation, the obtained biochemical profile was analyzed with the ApiWeb™ online software (https://apiweb-.biomerieux.com).

The best-performing strain was analyzed for its fermentative capacity on the 49 carbohydrates constituting the API 50 CHL gallery. A positive result corresponded to a yellow turn in the pH indicator: bromocresol purple (acidification of the medium due to the fermentation of the sugar tested), with the exception of the esculin tubule, which becomes black if the result is positive.

This profile was analyzed by the Identax Bacterial identification system software (www.identax.org). On the basis of this analysis, the obtained results revealed that the producing strain has a 99.52% homology with *L. paracasei*.

4. Effect of Proteases and Lipases on the Antibacterial Activity

The effect of different enzymes on the antibacterial activity of the supernatant was tested under optimal conditions. Thus, 100 µL aliquots of the supernatant were mixed with 100 µL of enzymes solution prepared at a concentration of 2 mg/mL in 0.05M of buffer and at appropriate pH for each enzyme and then sterilized by filtration. The used enzymes and their operating conditions are presented in Table 1 below. Table 1 shows the used enzymes and their operating conditions.

TABLE 1

| Enzymes | Buffers | pH |
|---|---|---|
| Pepsin (Sigma-Aldrich, USA) | Sodium citrate | 3.0 |
| Trypsin (Sigma-Aldrich, USA) | Sodium phosphate | 7.0 |
| Papain (Merck, USA) | Sodium phosphate | 7.0 |
| α-chymotrypsin (Sigma-Aldrich, USA) | Sodium phosphate | 7.0 |
| Proteinase K (Sigma-Aldrich, USA) | Tris-HCl | 7.0 |
| α-amylase (Merck, USA) | Sodium phosphate | 7.0 |
| Catalase (Merck, USA) | Sodium phosphate | 7.0 |
| Lipase (Sigma-Aldrich, USA) | Sodium phosphate | 7.0 |

After incubation at 37° C. for 2 h, samples were boiled for 3 min in a water bath and immediately cooled to 4° C. to inactivate the enzyme. The residual antibacterial activity of these samples, adjusted to pH 5 (with 1M NaOH or 1M HCl), sterilized by filtration and concentrated to approximately 100 µL, was tested against *E. coli* ATCC8739 and *E. coli* 184 by the well diffusion method. A sample of a sterile MRS broth treated under similar conditions was used as a negative control.

The nature of the active antibacterial compound(s) produced by the LAB strain was determined regarding the remaining activity after enzyme treatment by well diffusion method. The antibacterial activity was attributed to proteinaceous compounds if proteolytic enzymes induce the loss of the related activity, in comparison with inhibition zones diameter displayed by the untreated control (17 mm). A partial loss of activity was observed for supernatant treated with pepsin, trypsin and α-chymotrypsin; this loss was revealed by a decrease of the inhibition zone diameters of the samples treated with these enzymes with average inhibition zones equal to 8.16, 10.16 and 8.83 mm, respectively. Moreover, the antibacterial activity was completely lost after treatment with papain and proteinase K. These results suggest that the antibacterial activity was not due to hydrogen peroxide, or any substance of lipidic or polysaccharidic nature, but very likely attributed to a proteinaceous substance (see Table 2). As a matter of fact, the antibacterial activity associated with *L. paracasei* is at least, but not last a bacteriocin. This strain was registered and deposited at Pasteur Culture collection under reference CNCM I-5369. Table 2 shows the effect of enzymes and pH on anti-*E. coli* activity of *L. paracasei* CNCM I-5369 culture supernatant.

TABLE 2

| Treatments | Activity |
|---|---|
| Pepsin (2 mg/mL) | + |
| α-chemotrypsin (2 mg/mL) | + |
| Papain (2 mg/mL) | − |
| Proteinase K (2 mg/mL) | − |
| Trypsin (2 mg/mL) | + |
| α-amylase (2 mg/mL) | + |
| Lipase (2 mg/mL) | + |
| pH 2 to 5 | + |
| pH 6 | +/− |
| pH 7 to 10 | − |

5. Stability of Bacteriocin(s) Produced by *L. paracasei* I-CNCM 5369 (LAB Strain) Following a Heat Treatment and a Storage Process The supernatant, obtained by centrifugation (8000 g. 4° C., 10 min) from a fresh culture of *L. paracasei* I-CNCM 5369, was heat-treated at 80° C., 90° C. and 100° C. for 5, 10, 15, 20, 30, 60 and 120 min. The antibacterial activity, determined by well diffusion method, remained unchanged after 5 min of heat-treatment at 80° C. and 90° C., but not at 100° C. Then the effect appeared to be temperature dependent, and the activity decreased over time (Table 3). Table 3 shows the results of the activity of *L. paracasei* CNCM I-5369 culture supernatant heat treated.

TABLE 3

| Treatment | 5 min | 10 min | 15 min | 20 min | 30 min | 60 min | 120 min |
|---|---|---|---|---|---|---|---|
| Untreated (room temperature) | ++ | ++ | ++ | ++ | ++ | + | + |
| 80° C. | ++ | ++ | ++ | + | + | + | +/− |
| 90° C. | ++ | + | + | + | + | +/− | − |
| 100° C. | + | + | + | + | +/− | − | − |

−: No inhibition;
+/−: 0-1 mm;
+: 1-3 mm;
++: 3 to 6 mm;
+++: >6 mm

The stability of *L. paracasei* I-CNCM 5369 antibacterial activity (anti-*E. coli*) was assessed during refrigeration, freezing and lyophilized conditions. The storage at 4° C. had almost no effect on the anti-*E. coli* activity of *L. paracasei* I-CNCM 5369 since the total activity registered in arbitrary units/mL (AU/mL) was similar to that of the freshly pre- pared supernatant. Noteworthy, this activity remained stable at 4° C. whatever was the time of storage. Nevertheless, the freezing and lyophilized conditions altered significantly this activity, as shown in Table 4. Table 4 depicts the results of the activity of *L. paracasei* I-CNCM 5369 culture superna- tant under different storage conditions.

TABLE 4

| Fractions | anti *E. coli* 184 activity |
|---|---|
| Fresh Supernatant | 400 AU/mL |
| Supernatant stored at 4° C. (2-4 h) | 400 AU/mL |
| Supernatant stored at 4° C. (48-72 h) | 400 AU/mL |
| Supernatant stored at 4° C. (>72 h) | 400 AU/mL |
| Supernatant frozen-thawed (−20° C.) | 200 à 400 AU/mL |
| Supernatant lyophilized | 200 AU/mL |

6. Kinetic of Production of Putative Anti-*E. coli* Bacteriocin(s) by *L. paracasei* CNCM I-5369

Figure 1:
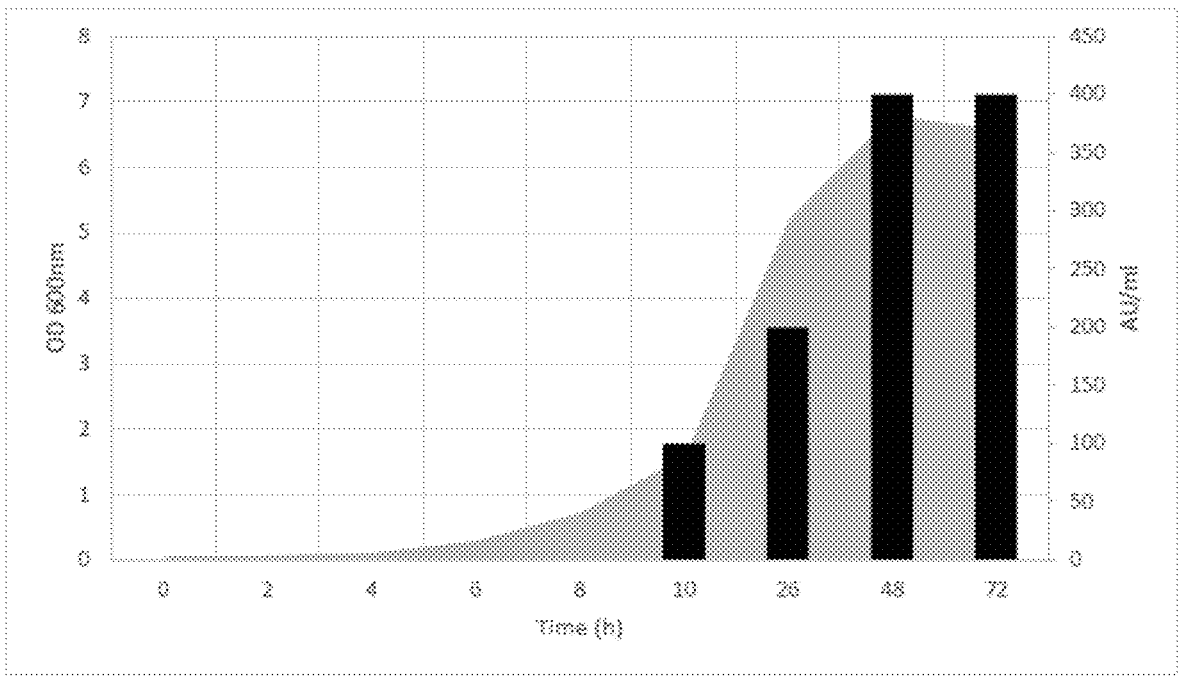
FIG. 1 shows the kinetics of anti-*E. coli* activity in the culture supernatant of *L. paracasei* CNCM I-5369 expressed by AU/mL (arbitrary unit histogram), with the monitoring of OD of the bacterial growth at 600 nm (grey area)

The kinetics of production of the putative bacteriocin(s) endowed with anti-*E. coli* activity by *L. paracasei* I-CNCM 5369 was evaluated using the arbitrary units per mL (AU/ mL), upon the growth of the bacteriocinogenic strain in MRS medium at 37° C. for 72 h. The culture supernatant, collected at one-hour interval, was serially diluted in MRS medium according to the following dilution ratio: 1/2, 1/4, 1/8, 1/16, 1/32 and 1/64. 50 μL of each of these diluted supernatant fractions were deposited on semi-solid Brain Heart Infusion (BHI) medium (containing 1% agar) previ- ously inoculated with the indicator strain, *E. coli* 184 carrying mcr-1 gene, responsible of colistin resistance. The petri dishes were incubated at 4° C. for 1 h and then at 37° C. for 18 h. The antibacterial activity was then determined in arbitrary units per milliliter of culture medium (AU/mL). Concomitantly, the optical density of the culture at 600 nm was monitored during the same experiment time intervals, using a spectrophotometer, with sterile MRS medium as blank. Based on the data depicted in FIG. 1, the production of the putative bacteriocin(s) appeared to be correlated with the bacterial growth of the bacteriocinogenic strain, increas- ing therefore progressively during 48 h of growth.

7. Purification of the Active Extract E20 Fraction from a Culture Supernatant of *L. paracasei* I-CNCM 5369

The cell-free supernatant (CFS) was obtained by centrifu- gation (8 000 g, 10 min, 4° C.) of a culture of *L. paracasei* I-CNCM 5369 grown without shaking on MRS medium for 24 to 30 h at 37° C. Then 40 mL of the obtained CFS was loaded onto a reversed phase C18 (Agilent, USA) cartridge. Afterwards, a washing step was performed with 10% (v/v) acetonitrile followed-up by an elution with 40 mL of 20% (v/v) acetonitrile solution in order to eluate the active fraction. The active fraction was dried using SpeedVac and resuspended in 1:10 of the initial volume of ultrapure water. The resulting active solution was designed as fraction E20 (or E20% particularly in the figures) throughout the text. Fraction E20 was stored at 4° C. and therefore used for the different tests to characterize the anti-*E. coli* activity. Noteworthy, E20 fraction was tested against a panel of *E. coli* strains with different genotypes to examine their sensibility to the putative bacteriocin(s) contained in this fraction. This assessment was performed by the determination of the minimal inhibitory concentration (MIC) values, which were ranging from 250 to 2 000 μg/mL (Table 5). Interestingly *E. coli* 184 and ATCC8739 strains exhibited the same E20 fraction MIC values, whereas the colistin MIC was four folds higher than for the *E. coli* 184 strain compared to the reference strain *E. coli* ATCC8739. Table 5 displays the MIC values attributable to E20 fraction obtained from the culture supernatant of *L. paracasei* I-CNCM 5369 against a panel of *E. coli* strains.

TABLE 5

| Strains | E20 fraction (MIC μg/mL) | Colistin (MIC μg/mL) | Genotypes and sources |
|---|---|---|---|
| *E. coli* 184 | 1 000 | 8 | mcr-1[+] |
| *E. coli* 289 | 2 000 | 8 | mcr-1[−] |
| *E. coli* ATCC8739 | 1 000 | 2 | Reference strain |
| *E. coli* CIP7628 | 1 000 | 1 | Reference strain |
| *E. coli* SBS36 | 250 | 2 | Truncated LPS |
| *E. coli* TOP10 | 1 000 | 1 | LPS- |
| *E. coli* E4A4 WT | 1 000 | 2 | Environmental strain |
| *E. coli* E4A4 variant | 1 000 | 16 | Colistin unsensibilised variant |

8. Bactericidal Activities and Killing Curves Analyses

The killing curves were determined on three *E. coli* strains, because of for their resistance or sensitivity to colistin. These strains were *E. coli* 184 (mcr-1), *E. coli* E4A4 variant with resistance to colistin, and *E. coli* ATCC8739 colistin-sensitive reference strain (Table 5). These strains were inoculated in BHI (Brain Heart Infusion) medium containing the semi-purified fraction of E20 fraction at inhibitory concentration. An untreated *E. coli* ATCC8739 control treated with inhibitory concentration of colistin (16 μg/mL) was also tested. The pH of the medium was adjusted to 4.5-5 in the various samples, which were incubated at 37° C. for 8 h. At regular intervals of time, samples were taken to determine the number of colony forming units per mL (CFU/mL) under each tested condition.

Figure 2:
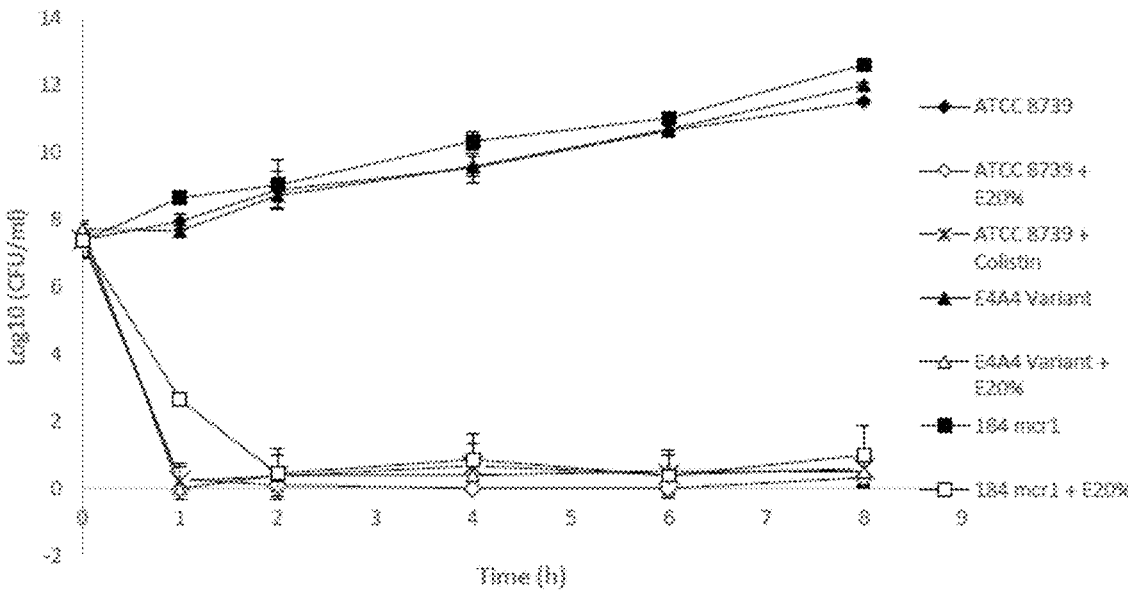
FIG. 2 exhibits the killing curves (or survival curves) of several selected *E. coli* strains treated with E20 fraction.

As depicted in the FIG. 2, the number of CFU/mL of the strains treated with E20 fraction decreased rapidly with no visible growth (0 CFU/mL), after 1 h of incubation. How- ever, *E. coli* 184 showed similar behavior after 2 h of incubation. A similar data was obtained after 1 h of incu- bation for *E. coli* ATCC8739 treated with colistin (16 μg/mL). Of note, untreated strains used as controls exhib- ited, as expected, normal occurring growth curves along the experiment (see FIG. 2).

9. Synergistic Interaction Between Colistin and E20 Frac- tion

E20 fraction prepared from *L. paracasei* I-CNCM 5369, was half-diluted and mixed with colistin at a concentration ranging from 1 to 128 μg/mL in BHI medium. The resulting formulations were tested against *E. coli* 184, carrying the mcr-1 gene, as well as on other *E. coli* strains (Table 6). After an overnight period of incubation at 37° C., the growth of *E. coli* strains was checked by spectrophotometry at $OD_{600\ nm}$, and new MIC values of colistin/E20 were determined. Importantly, the combination of E20 fraction with colistin decreased the MIC values, at least four times, compared to the MIC obtained with colistin alone. Indeed, the decreased from 8 to 2 µg/mL in the presence of E20 fraction. This synergetic interaction was as well observed for other *E. coli* strains, where the MIC values decreased twice for *E. coli* E4A4WT, 4 times folds for *E. coli* 289 and 8 times for *E. coli* E4A4 variant. It should be noted that *E. coli* strains ATCC8739, SBS36 and TOP10 did not show any reduction of the MIC value for the antibiotic (see Table 6). Table 6 exhibits the MIC values obtained for colistin alone and in combination with E20 fraction on different *E. coli* strains. The weight composition of the mixture of E20 fraction+ colistin is indicated in brackets next to the MIC value. The first value refers to the amount of colistin in µg/mL, whereas the second in brackets refers to the amount of E20 fraction in µg/mL).

TABLE 6

| Strains | Colistin (MIC µg/mL) | Colistin + E20 fraction (MIC µg/mL) |
|---|---|---|
| *E. coli* 184 | 8 | 252 (2: (250)) |
| *E. coli* 289 | 8 | 502 (2: (500)) |
| *E. coli* ATCC8739 | 2 | 252 (2: (250)) |
| *E. coli* SBS36 | 2 | 252 (2: (250)) |
| *E. coli* TOP10 | 1 | 251 (1: (250)) |
| *E. coli* E4A4 WT | 2 | 251 (1: (250)) |
| *E. coli* E4A4 variant | 16 | 252 (2: (250)) |

According to the results of Table 6, a mixture containing at least 99% of E20 and 1% of colistin can be as efficient as colistin alone in several strains and even colistin resistant strains. Further, the combination of E20 with colistin enables the reduction of the amount of E20 and the reduction of the amount of the mixture E20+colistin itself.

10. Cytotoxicity Assay

Figure 3:
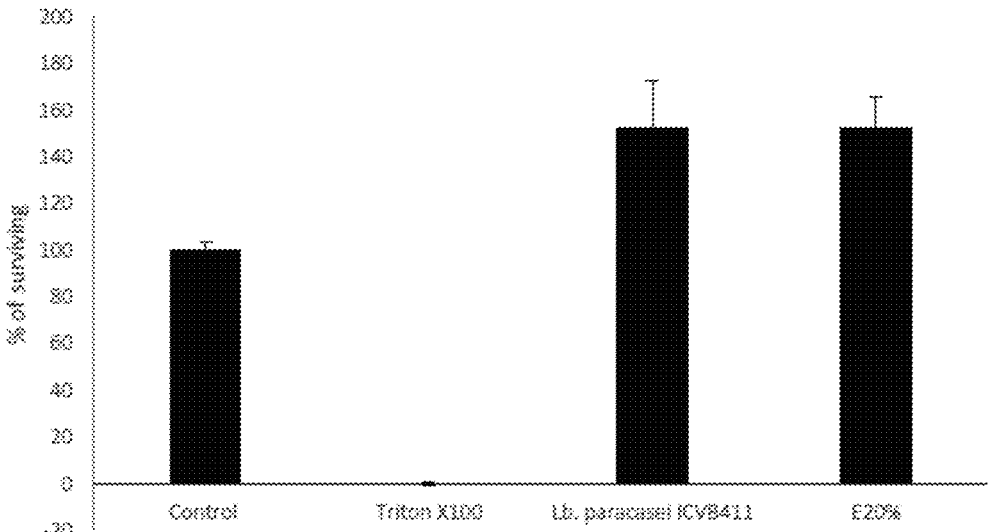
FIG. 3 displays the cytotoxicity of *L. paracasei* CNCM I-5369 and E20 fraction on IPEC-1 cells.

The cytotoxicity of E20 fraction was evaluated in-vitro on intestinal porcine epithelial cells (IPEC-1). The cytotoxicity assay was therefore performed using IPEC-1 cells cultivated on 96-well tissue culture plates at 37° C. for 48 to 72 h, under 5% $CO_2$ atmosphere, until formation of a confluent cell culture on the bottom of each well. Cells of *L. paracasei* I-CNCM 5369, harvested from a 24 to 30 h old culture in MRS medium, and semi-purified E20 fraction were tested after being diluted one hundred and four folds, respectively, in DMEM (Dulbecco's Modified Eagle's Medium) medium without antibiotics and serum. DMEM medium without antibiotic or serum were tested as controls. The plate containing IPEC-1 cells treated with diluted CFS and E20 samples, as described previously, were incubated for 24 h at 37° C., in 5% $CO_2$ atmosphere. CCK-8 assay (Dojindo Molecular Technologies, Japan), based on the reduction of tetrazolium salt by active mitochondria, was used to assess cell viability of the treated IPEC-1 cells. 150 µL of DMEM containing 7.5 µL of CCK-8 reagent were added in each well and cells were incubated for 2 h. Plates were read at 450 nm in a microplate reader spectrophotometer (Xenius, Safas, Monaco). Results were expressed in % of basal growth observed with non-treated cells (see FIG. 3). The results in FIG. 3 show that E20 fraction is not toxic towards intestinal porcine epithelial cells (IPEC-1) since the % of survival is equal to 150% for IPEC-1 cells treated with E20 fraction.

11. Loading E20 Fraction on Alginate Nanoparticles (Alg NPs/E20)

A. Preparation of Alginate Nanoparticles (Alg NPs) and Characterization Thereof

Preparation

The Alg NPs were prepared using a cost-effective technique through planetary ball milling. In this technique, bulk powder sodium alginate (Sigma-Aldrich, W201502) sample was used to prepare Alg NPs. Milling was performed at room temperature in a polytetrafluoroethylene (PTFE) vial (volume=50 mL) using 2 g of sodium alginate and 13 hardened steel balls (total weight=112 g; 10 balls of 10 mm+3 balls of 20 mm in diameter). The milling process lasted for 10 h using a rotation speed of 440 rpm. At the end of the milling process, the Alg NPs were collected and dissolved in Milli-Q water (0.5 mg/mL) under ultrasonication (BRANSON 2800, frequency: 40 KHz) for 1 h at 25° C.

The alginate nanoparticles (0.5 mg/mL) are stable over than 3 months at +4° C. without any apparent precipitation or aggregation.

Characterization of Alginate Nanoparticles (Alg NPs)

The Alg NPs were characterized using different techniques such as dynamic light scattering (DLS), scanning electron microscopy (SEM), Fourier transform infrared (FTIR) spectroscopy, and thermogravimetric analysis (TGA) measurements.

Scanning Electron Microscopy (SEM)

Figure 4:
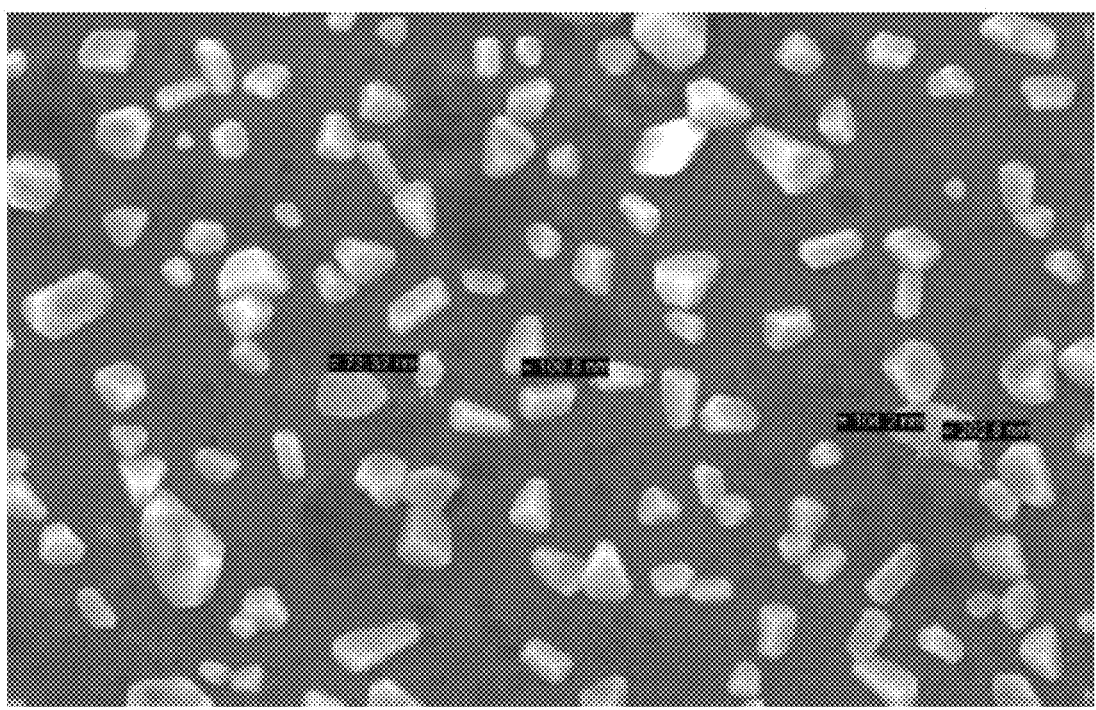
FIG. 4 is an SEM image of Alg NPs (sodium alginate nanoparticles).

The morphology of the samples was examined by an ULTRA 55 (Zeiss, France) Scanning Electron Microscope (SEM). The samples for SEM analysis are prepared by depositing a few drops of an aqueous solution of Alg NPs (500 µg·mL$^{-1}$) on a clean silicon substrate, followed by water evaporation at 100° C. for 1 h. The results are shown in FIG. 4.

SEM analysis shows nanoparticles with a wide size distribution (50-200 nm).

Dynamic Light Scattering (DLS) Measurements

Figure 5A:
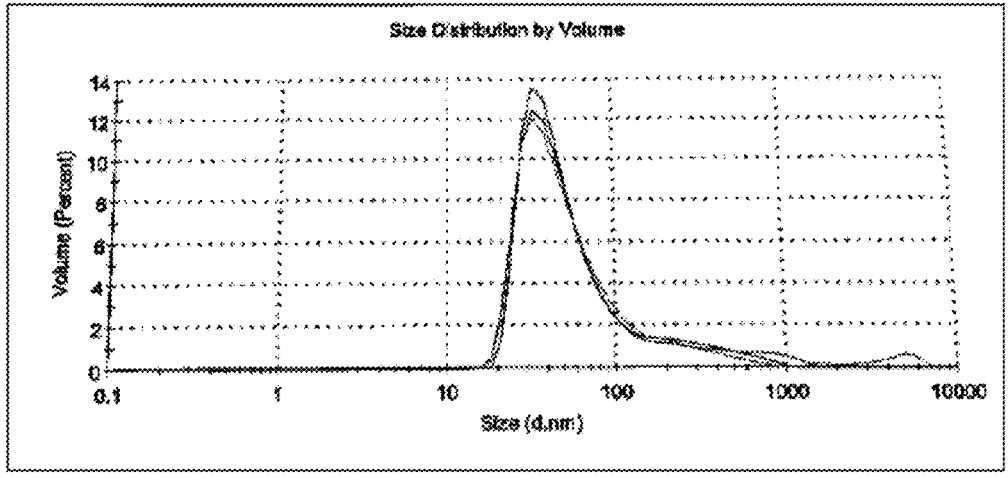
FIGS. 5A and 5B show the DLS (size distribution by volume) and zeta potential distribution measurements of Alg NPs (500 μg·mL⁻¹) in water.
Figure 5B:
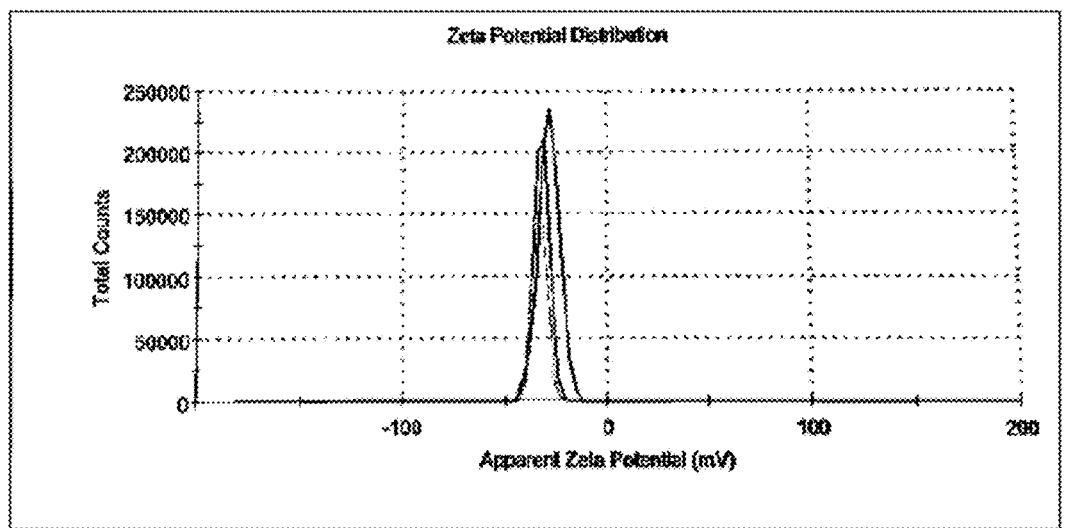

The hydrodynamic size and surface charge of the synthesized nanocomposite were determined using dynamic light scattering principle (Malvern Zetasizer, NanoZS) at 25° C. Solutions were freshly prepared before analysis, and the reported data are means for three independent measurements. DLS measurements shown in FIG. 5A revealed nanoparticles with an average size of 118 nm with a zeta potential of −32 mV at pH 7.2 (at pH 5, the zeta potential is −12 mV) (see FIG. 5B), indicating that the Alg NPs are negatively charged.

Thermogravimetric Analysis (TGA)

Thermogravimetric analysis (TGA/DTG) was carried out on a TG/DTG NETZSCH TG 209 F3 instrument. Thermograms were recorded by loading 10 mg of alginate nanoparticles and subjecting the sample to a heating rate of 10° C./min from 30° C. to 980° C. under nitrogen atmosphere.

Figure 6:
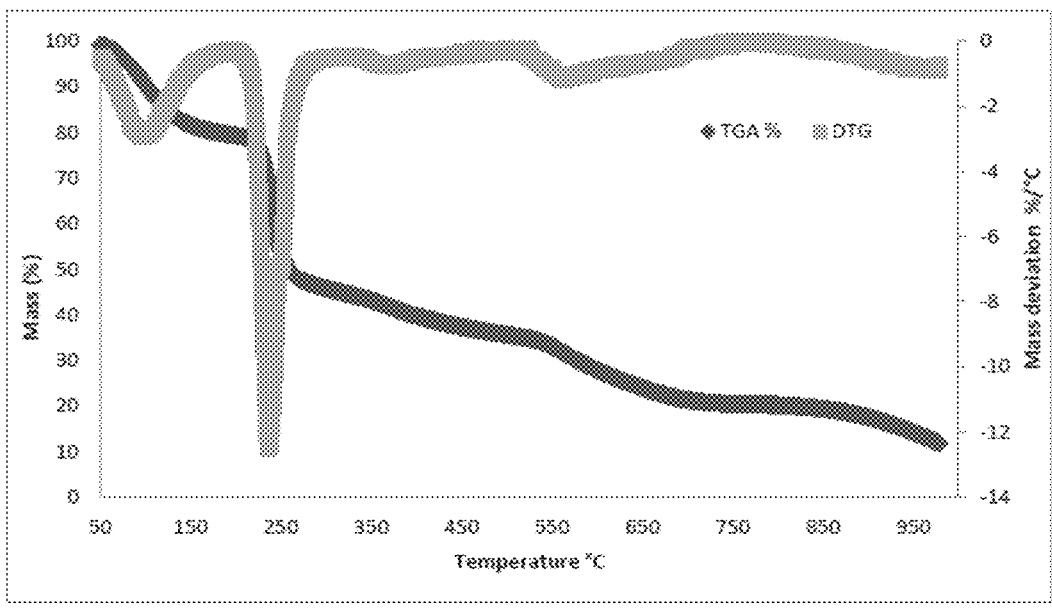
FIG. 6 depicts the thermal behaviour of Alg NPs, showing different weight losses according to temperature (in ° C.)
Figure 7:
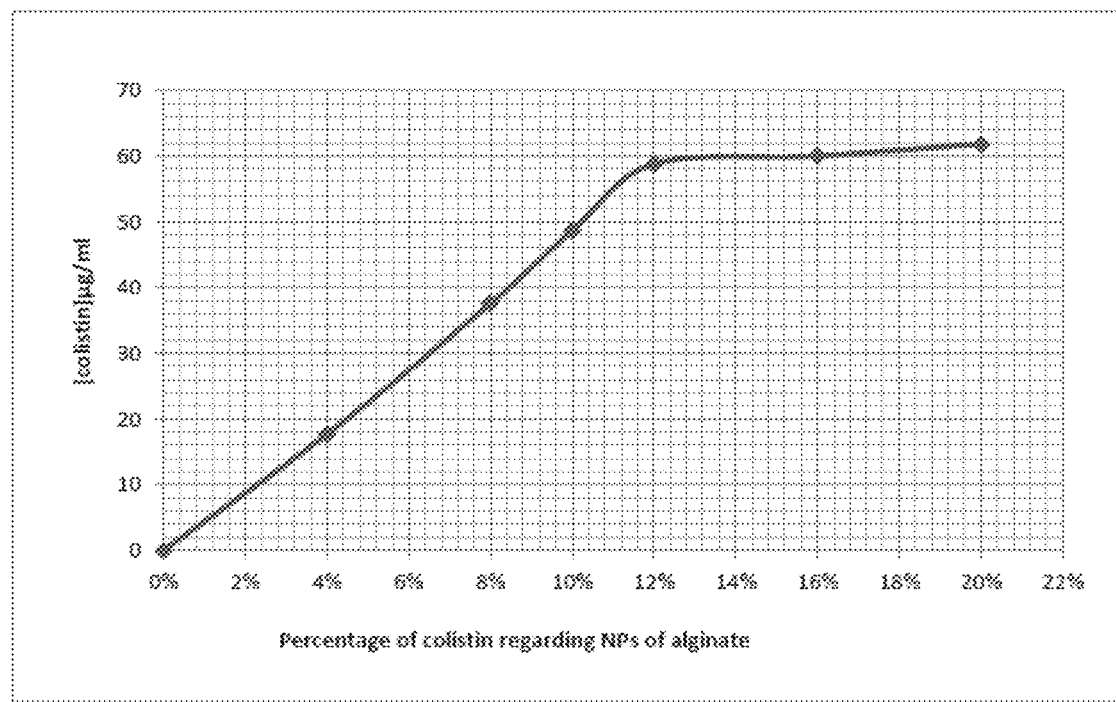
FIG. 7 shows the quantification of the amount of colistin (μg/mL) adsorbed on/in alginate nanoparticles (500 μg/mL) (colistin μg/mL versus mass of colistin/mass of alginate nanoparticles×100)
Figure 8:
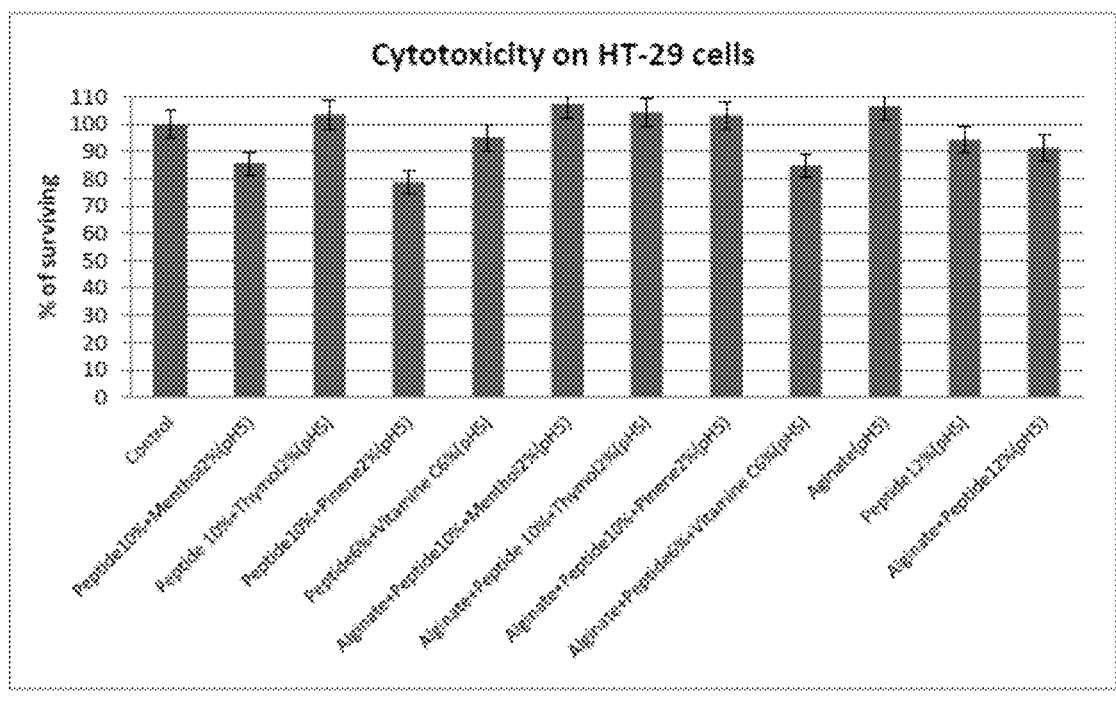
FIG. 8 to FIG. 11 show the results regarding the cell toxicity of Alg NPs on several cell lines; the term "peptide" refers to E20 fraction and "alginate" to Alg NPs.
Figure 9:
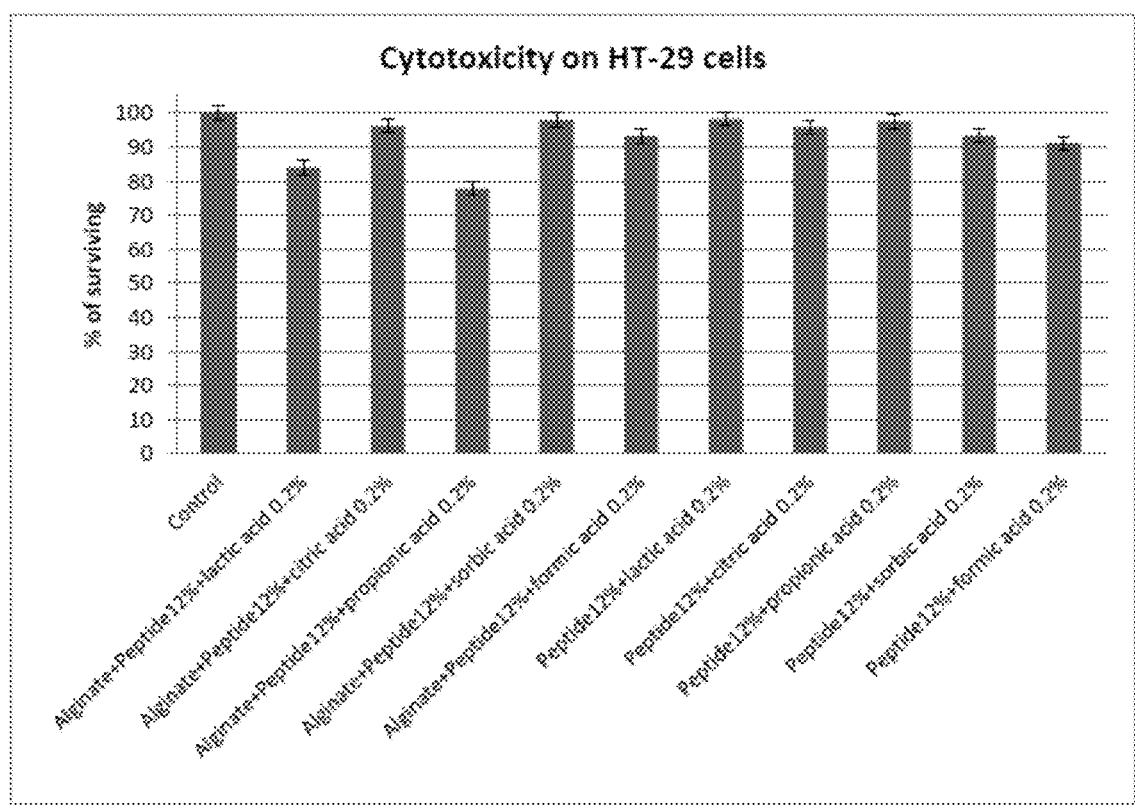
Figure 10:
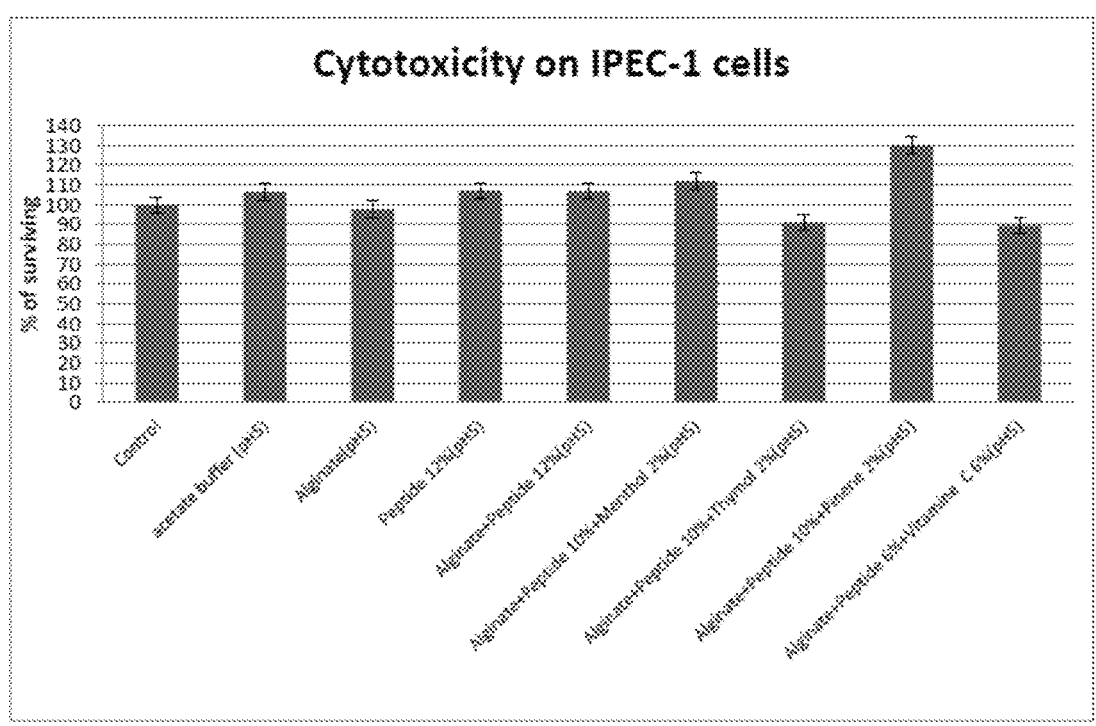
Figure 11:
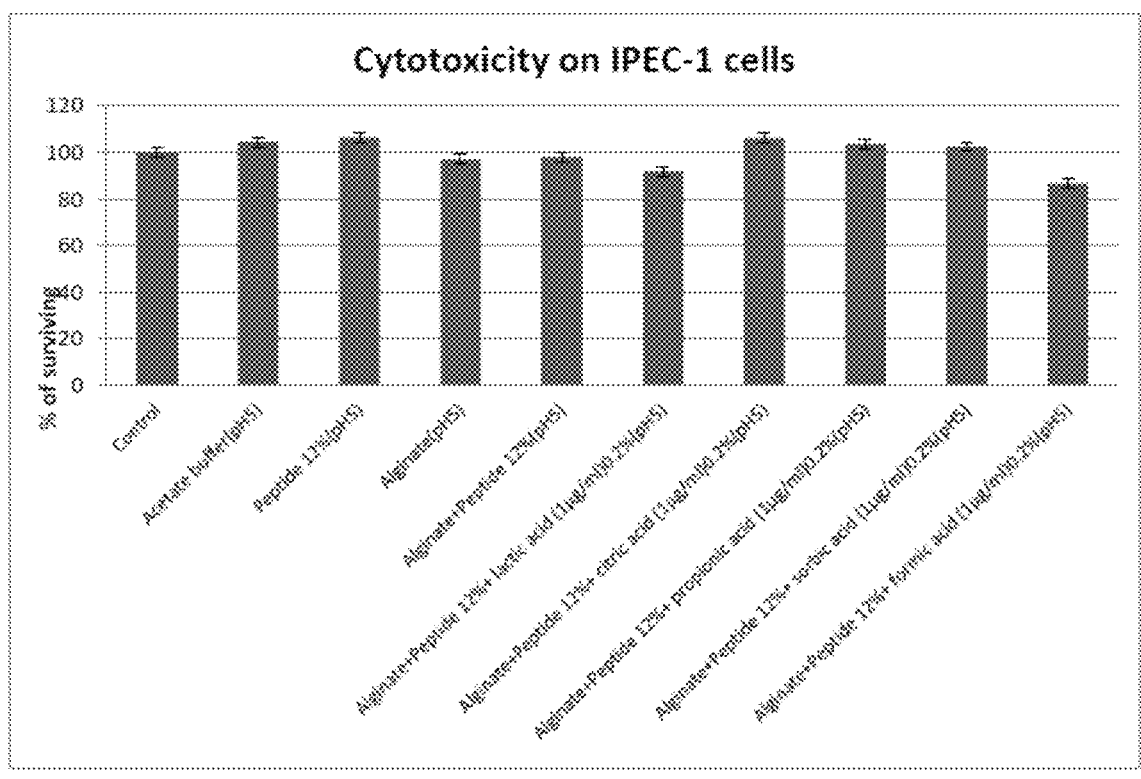

FIG. 6 depicts the thermal behaviour of Alg NPs, showing different weight losses. The first weight loss (<100° C.) corresponds to water desorption from the nanoparticles surface. A second sharp weight loss occurs between 200 and 250° C. and can be assigned to the decomposition of the polymer chains of the nanoparticles. Thereafter, a steady and continuous weight loss is observed with a residual mass <15% at 980° C.

Fourier-Transform Infrared (FTIR) Spectroscopy

Fourier transform infrared spectroscopy (FTIR) was performed on a Thermo Fisher Inc, Nicolet 380. The samples were analysed in the IR radiation in a pallet form, which is made by mixing 1 mg of Alg NPs with 100 mg of potassium bromide (KBr). The mixture was then grinded properly to ensure uniform distribution in the KBr base. Finally, the grinded mixture is pressed in a hydraulic press by applying a pressure of ~7 to 9 tons. The chemical composition of Alg NPs was further assessed by Fourier transform infrared spectroscopy (FTIR). The FTIR spectrum of sodium alginate precursor comprises the characteristic vibration bands of hydroxyl, ether and carboxylic functional groups. The broad and strong vibration peak at 3431 cm$^{-1}$ is assigned the stretching vibration of O—H bonds. Stretching vibrations of aliphatic C—H groups are observed at 2920 and 2850 cm$^{-1}$. The bands at 1625 and 1414 cm$^{-1}$ are ascribed to asymmetric and symmetric stretching vibrations of carboxylate salt ion, respectively. The peak at 1032 cm$^{-1}$ is due to C—O vibrations.

The FTIR spectrum of Alg NPs consists of similar bands, indicating that the chemical composition and structure of the alginate precursor was not altered during nanoparticles' formation using ball milling process (results not shown).
Characterization of Alginate Nanoparticles/E20 Fraction (Alg NPs/E20)

Loading E20 onto alginate nanoparticles did not impact much their size as seen in Table 7. Indeed, DLS measurements revealed an average size of Alg NPs of 118 nm at pH 7, comparable to 120 nm recorded at pH 5. A slight size increase (4 nm) was observed upon loading E20 fraction on Alg NPs, which is a good indication on peptide adsorption on the nanoparticles' surface. The results are corroborated by zeta potential measurements. The surface of Alg NPs is negatively charged (−32 mV at pH 7) and (−12 mV at pH 5) and becomes neutral upon E20 loading. Table 7 shows the size and surface charge of Alg NPs before and after loading E20 fraction on their surface.

TABLE 7

|  | Size (nm) | Charge (mV) |
| --- | --- | --- |
| Alg-NPs, pH 7 | 118 | −32 |
| Alg-NPs, pH 5 | 120 | −12 |
| Alg-NPs + E20, pH 5 | 124 | −0.5 |
| Alg-NPs + E20, pH 5.4 | 124 | 0.0 |

Determination of Adsorption Capacity of Alg NPs for E20 Fraction

The determination of the maximum amount of E20 that can be loaded on Alg NPs is an important parameter to distinguish between the activity of free E20 fraction from that adsorbed on Alg NPs. This has been done based on the results obtained for colistin loading on Alg NPs. The amount of colistin adsorbed on Alg NPs was assessed using HPLC. Different solutions of Alg NPs/colistin were prepared by mixing Alg NPs (500 µg/mL in water) with colistin (20, 40, 50, 60, 80 and 100 µg/mL) and subjected to ultrasonication for 60 min at RT. Each mixture was dialyzed for 24 h at RT using 8 kDa membrane (the water is changed every 6 h), and the amount of colistin in the solution was determined by HPLC. From FIG. 8, we can conclude that the maximum of colistin that can be adsorbed on 500 µg/mL Alg NPs is 60 µg. This corresponds to 12% by weight. In the whole study we have the total amount of 60 µg for E20 or E20+small molecules (herein after called "component") and 500 µg/mL Alg NPs to investigate the antibacterial activity of different formulations.
Cytotoxicity Studies The cytotoxicity of the different formulations (Alg NPs, Alg NPs+E20, Alg NPs+E20+small molecule) was evaluated in-vitro towards human colon cancer (HT-29) and intestinal porcine epithelial cells (IPEC-1). The cytotoxicity assay was therefore performed using HT-29 and IPEC-1 cell lines cultivated on 96-well tissue culture plates at 37° C. for 48 to 72 h, under 5% $CO_2$ atmosphere, until formation of a confluent cell culture on the bottom of each well. Different formulations and semi-purified E20 fraction were tested in DMEM (Dulbecco's Modified Eagle's Medium) medium without antibiotics and serum. DMEM medium without antibiotic or serum were tested as controls. The plate containing HT-29 and IPEC-1 cells treated with the different formulations, as described previously, were incubated for 24 h at 37° C., in 5% $CO_2$ atmosphere. CCK-8 assay (Dojindo Molecular Technologies, Japan), based on the reduction of tetrazolium salt by active mitochondria, was used to assess cell viability of the treated HT-29 or IPEC-1 cells. 150 µL of DMEM containing 7.5 µL of CCK-8 reagent were added in each well and cells were incubated for 2 h. Plates were read at 450 nm in a microplate reader spectrophotometer (Xenius, Safas, Monaco). Results were expressed in % of basal growth observed with non-treated cells (FIGS. 8-11).

The results in FIGS. 8-11 reveal that Alg NPs do not exhibit any apparent cytotoxicity on the investigated cell lines. Similarly, free E20 (12%), and E20 and E20+small molecules loaded on Alg nanoparticles do not have obvious cytotoxic effect on HT-29 and IPEC-1 cell lines.
Biological Activity of the Combination of Alg NPs and E20

The alginate nanoparticles (Alg NPs) were obtained by a top down process (ball milling) and used at a concentration of 500 µg/mL. The E20 fraction was mixed at a concentration of 60 µg/mL with this suspension, which corresponds to 12% of the used Alg NPs concentration. This mixture was adjusted to pH 5 by addition of acetic acid and tested against the target strains listed in Table 8. From the results in Table 8, the activity has significantly increased comparatively to that obtained with the E20 fraction alone. To gain insights on the effects of alginate nanoparticles, colistin was also loaded on Alg NPs and the resulting formulation (colistin-Alg NPs) was tested against same target *E. coli* strains. As a consequence, the MIC values have significantly decreased comparatively to that obtained with colistin alone; this effect was particularly notable for *E. coli* 184 and 289 strains displaying resistance to colistin (Table 8).

Furthermore, we tested the effects of lactic acid as well as those of menthol and thymol (essential oils) at a low concentration of 2%. Regarding the MIC values, we concluded that these molecules including organic acids and essential oils can be of interest and their combination with E20 fraction and colistin deserve to be investigated. Table 8 displays the results regarding the effect of different formulations based on the combination of Alg NPs and different molecules towards *E. coli* strains.

TABLE 8

| Strains | Alginate + colisitin (12%) (MIC colistin µg/mL) | Alginate + E20 (12%) (MIC E20 µg/mL) | Alginate + E20 (12%) + Lactic acid 0.2% (MIC E20 µg/mL) | Alginate + E20 (10%) + Menthol 2% (MIC E20 µg/mL) | Alginate + E20 (10%) + Thymol 2% (MIC E20 µg/mL) |
| --- | --- | --- | --- | --- | --- |
| *E. coli* 184 | 4 | 4 | 2 | 1 | 1 |
| *E. coli* 289 | 4 | 4 | 2 | 4 | 1 |
| *E. coli* ATCC8739 | 1 | 2 | 0.5 | 0.5 | 0.5 |
| *E. coli* CIP7628 | 1 | 2 | 2 | 0.5 | 0.5 |
| *E. coli* SBS36 | 1 | 2 | 1 | 0.5 | 0.5 |

TABLE 8-continued

| Strains | Alginate + colisitin (12%) (MIC colistin μg/mL) | Alginate + E20 (12%) (MIC E20 μg/mL) | Alginate + E20 (12%) + Lactic acid 0.2% (MIC E20 μg/mL) | Alginate + E20 (10%) + Menthol 2% (MIC E20 μg/mL) | Alginate + E20 (10%) + Thymol 2% (MIC E20 μg/mL) |
|---|---|---|---|---|---|
| E. coli TOP10 | 0.5 | 2 | 0.5 | 0.5 | 0.5 |
| E. coli E4A4 WT | 2 | 2 | 2 | 1 | 0.5 |
| E. coli E4A4 Variant | 4 | 2 | 2 | 2 | 2 |

Importantly, the anti-*E. coli* activity ascribed to E20 fraction produced by *L. paracasei* I-CNCM 5369 was tightly pH dependent. Indeed, the activity was observed only at pH 4.5 to pH 5. This restricted pH activity can be crippling for any application because of the different pH values encountered in the gastrointestinal compartments of pigs, mainly in piglets after weaning.

Thus, the formulations based on the Alg NPs/antimicrobials either alone or in combination with essential oils or lactic acid were tested at different pH values.

Indeed, the different formulations were tested at pH values 6 and 7, and then incubated at pH 2 for 2 h and tested again at pH 5 and pH 7, which correspond to the pH values encountered during the passage through the esophagus, stomach and duodenum. It appeared thereafter that the activity of the different formulations tested has decreased when the pH was higher than pH 5, with MIC values of 16 μg/mL and 32 μg/mL at pH 6 and 7, respectively, instead of 4 μg/mL at pH of 5. However, the combination with lactic acid, at 0.2%, by weight or essential oils either menthol or thymol, at 2 or 4% by weight permitted to keep MIC values of 2 to 4 μg/mL, independently of the pH values (see Table 9). Table 9 shows the results regarding the effects of pH on antagonist activities of Alg NPs associated with E20 and lactic acid or essential oils on *E. coli* 184 (mcr-1) strain.

TABLE 9

| | MIC E20 fraction (μg/mL) | | | |
|---|---|---|---|---|
| | pH 5 | pH 6 | pH 2 (2 h) then pH 7 | pH 2 (2 h) then pH 5 |
| Alg NPs | 4 | 16 | 32 | 4 |
| Alg NPs + E20(12%) + 0.2% lactic acid | 2 | 2 | 4 | 2 |
| Alg NPs + E20(10%) + 2% menthol | ≤2 | 2 | 4 | ≤2 |
| Alg NPs + E20(10%) + 2% thymol | ≤2 | 2 | 4 | ≤2 |
| Alg NPs + E20(10%) + 4% menthol | ≤2 | ≤2 | 4 | ≤2 |
| Alg NPs + E20(10%) + 4% thymol | ≤2 | ≤2 | 4 | ≤2 |

The formulations containing E20 fraction and Alg NPs associated with 2% or 4% essential oils (menthol or thymol) or 0.2% lactic acid, were subjected to successive action of digestive enzymes encountered in the digestive tract of piglet after weaning. A first incubation was carried out for 30 min at 39° C., with shaking (140 rpm) at pH 3 in presence of pepsin (15 U/mL), followed by a second incubation under similar temperature and agitation conditions at pH 6 and finally addition of chymotrypsin (5 U/mL) and trypsin (40 U/μL) followed by incubation for 2 h at 39° C., with shaking (140 rpm) at pH 6, according to the conditions described by Zhong et al. (see Zhong, R. Z., Xia, J. Q., Sun, H., Qin, G. X. (2017). Effects of different sources of protein on the growth performance, blood chemistry and polypeptide profiles in the gastrointestinal tract digesta of newly weaned piglets. J Anim Physiol Anim Nutr (Berl). 2017 October; 101(5):e312-e322. doi: 10.1111/jpn.12607).

During the first incubation, performed in the presence of pepsin at pH 3, the MIC values of fraction Alg NPs/E20 and Alg NPs/E20 associated with lactic acid, increased from 16 to 32 μg/mL and from 2 to 4 μg/mL, respectively (Table 10). Nevertheless, in the presence of essential oils at 2% or 4% by weight, the MIC values recorded were not different from those registered for the untreated formulations with enzymes, but incubated under similar conditions of temperature, agitation and pH. These results highlight that the combination of E20 fraction, Alg NPs and essential oils and/or lactic acid was robust enough to resist harsh simulated piglets' gastro-intestinal environment, marked by the drastic pH conditions, temperature and presence of digestive enzymes in the stomach and the first segment of the small intestine in the piglet. Table 10 summarizes the results regarding the effects of the digestive enzymes on the antagonistic activity of formulations based on alginate nanoparticles/E20 fractions associated with lactic acid or essential oils on *E. coli* 184 (mcr-1).

TABLE 10

| | MIC E20 fraction (μg/mL) | | |
|---|---|---|---|
| pH = 6 | Control (incubated without enzymes) | Treated with pepsin for 30 min (pH 3) then 2 h at pH 6 without trypsin and chymotrypsin* | Treated with pepsin for 30 min (pH 3) then 2 h at pH 6 with trypsin and chymotrypsin* |
| Alg NPs + E20 (12%) | 16 | 32 | 32 |
| Alg NPs + E20 (12%) + Lactic acid 0.2% | 2 | 4 | 4 |
| Alg NPs + E20(10%) + Menthol 2% | 4 | 4 | 4 |
| Alg NPs + E20(10%) + Thymol 2% | 2 | 2 | 2 |

*Incubation: 39° C. at 140 rpm/Pepsin 15 U/mL; Trypsin 40 U/μL; Chymotrypsin 5 U/ml 12. In-Silico Analysis of the Genome of *L. paracasei* I-CNCM 5369

Figure 12:
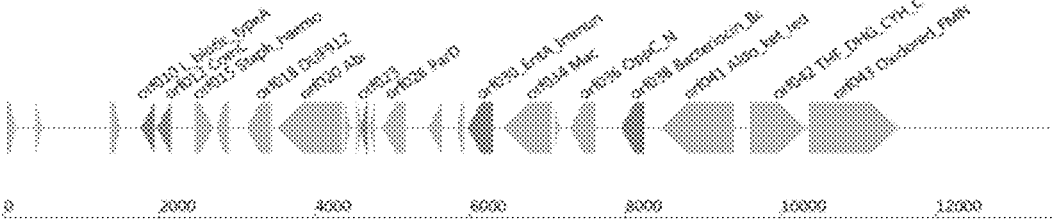
FIG. 12 shows the open reading frames (oft Open Reading Frame) potentially coding for bacteriocins through *L. paracasei* CNCM I-5369 genome analysis obtained with Bagel 3 online software.

In-silico analysis of the genome of *L. paracasei* I-CNCM 5369 using Bagel 3 online analysis software (bagel.molgenrug.nl) identified several open reading frames potentially encoding bacteriocin-like proteins (FIG. 12). Further analysis of the amino acid sequences translated from these genes using the Jpred software (www.compbio.dundee.ac.uk/jpred/) allowed the characterization of five peptides with predicted sizes of approximately 3.2 at 12 KDa (Table 11).

The first identified putative bacteriocin has a predicted size of 3,199 Da, with 29 amino acids, and possesses the characteristics of a class II bacteriocin and a pI of 5.17. The second and third putative bacteriocins have predicted sizes of 6,300 and 6,582 Da, with respectively 60 and 63 amino acids. These two peptides have estimated pI values of 4.86 and 8.25, respectively, and also belong to class II bacteriocins. The two largest open reading frames would potentially encode peptides larger than 10 kDa, more than 10,395 and 12,252 Da, with 101 and 111 amino acids, respectively. The calculated pIs are respectively 8.62 and 6. These last two predicted peptides belong also to class II bacteriocins (Table 11 shows the amino acid sequences of potential bacteriocins corresponding to the open reading frames (ORFs) identified by the online Bagel 3 software).

TABLE 11

| Class | ORF | peptide sequence |
|---|---|---|
| Class II | Orf010 | MYTMTNLKDKELSQITGGFAFVIPVAAILGFLASDAWSHADEIAGG ATSGWSLADKSHSL (SEQ ID NO 1) |
| Class II | Orf012 | MQQFMTLDNSSLEKIAGGENGGLWSIIGFGLGFSARSVLTGSLFV PSRGPVIDLVKQLTPKN (SEQ ID NO 2) |
| Class II | Orf023 | MLILGLIAIDAWSHTDQIIAGFLKGWQGM (SEQ ID NO 3) |
| Class II | Orf030 | MTDKRETLMSMLSKAYANPTIKAEPALRALIETNAKKVDEGDDEK AYVTAVTQLSHDISKYYLIHHAVPEELVAVFNYIKKDVPAADIDAAR YRAQALAAGLVAIPIVWGH (SEQ ID NO 4) |
| Class II | Orf038 | MYVKDSKVDLTQNNLLPFEEKRKIMSYNYRQLDDFQLSGVSGGK KKFDCAATFVTGITAGIGSGTITGLAGGPFGIIGGAVVGGNLGAVG SAIKCLGDGMQ (SEQ ID NO 5) |

Each of the orf coding for putative bacteriocin was cloned in expression vector suitable for *E. coli* competent cells. Each orf was cloned under the control of the inducible T7 promoter and with His-Tag (6 His) tail positioned on the N-terminal or C-terminal part. The cloning of each orf at the N- or C-terminal position of Histag tail, has led to 10 recombinant plasm ids. Each of these recombinant plasm ids was introduced in *E. coli* BL21 (DE3)(plysS) competent cells. The successfully transformed *E. coli* was regenerated in SOC medium for 1 h at 37° C. with shaking at 160 rpm, and then selected on Luria-Bertani (LB) agar medium supplemented with ampicillin (100 µg mL$^{-1}$) and chloramphenicol (30 µg mL$^{-1}$) (Sigma Aldrich). After overnight incubation at 37° C., the obtained colonies on LB agar medium with antibiotics were checked for the presence of the recombined plasmid containing the appropriate cloned orfs by PCR using specific primers.

Overnight culture of *E. coli* strain BL21(DE3)(pLysS), harboring each recombinant plasmid, was diluted to 1% (vol/vol) in LB medium containing ampicillin (100 µg mL$^{-1}$) and chloramphenicol (30 µg mL$^{-1}$) and then grown aerobically at 37° C. When the optical density had reached 0.8 at 600 nm, gene expression was induced by the addition of isopropyl-β-d-thiogalactopyranoside (IPTG) (Sigma) at a concentration of 1 mM. The cells were grown for another 5 h, and samples were harvested by centrifugation (8,000×g, 10 min, 4° C.) and the obtained cell pellets were kept after washing in PBS buffer. The cell pellets were then resuspended in PBS buffer containing 10 mM of imidazole (Sigma) at pH 7.9. The bacterial suspensions were sonicated 5 times for 2 min to disturb and lyse the cells. The separation of the cytoplasmic soluble fraction (CSF) from the cytoplasmic insoluble fraction and cell debris was performed by centrifugation (14,000×g, 15 min, 4° C.). The CSF was filtered (0.45-µm-pore-size filter) and then loaded directly onto a 1-mL nickel His-Trap chelating column (Amersham Biosciences). After loading, the column was successively washed with PBS containing 30 mM imidazole (pH 7.9). The peptides encoded by the cloned orfs with His-Tag were eluted with 2 mL of PBS containing 250 mM imidazole (pH 7.9).

Then the obtained solution was adjusted to pH 5 using acetic acid and then its activity (AU/mL) against *E. coli* colistin-resistant strain was evaluated, as described previously.

The results showed that all recombinant purified peptides on Ni-NTA columns have about 400 to 800 AU/mL. Interestingly, the N-terminal histagged recombinant peptide orf-38 exhibits better activity than its C-terminal histagged counterpart, 800 and 400 AU/mL, respectively.

Table 12 shows the results of the anti-*E. coli* activities (AU/mL) of recombinant peptides synthesized by heterologous expression in *E. coli* BL21 (DE3) (pLysS).

TABLE 12

| Recombinant peptide (N-terminal His-Tag) | anti *E. coli* activity | Recombinant peptide (C-terminal His-Tag) | anti *E. coli* activity |
|---|---|---|---|
| Orf10 HisTag N-ter | 400 AU/mL | Orf10 HisTag C-ter | 200 AU/mL |
| Orf12 HisTag N-ter | 400 AU/mL | Orf12 HisTag C-ter | 200 AU/mL |
| Orf23 HistTag N-ter | 400 AU/mL | Orf23 HistTag C-ter | 200 AU/mL |
| Orf30 HisTag N-ter | 400 AU/mL | Orf30 HisTag C-ter | 200 AU/mL |
| Orf38 HisTag N-Ter | 800 AU/mL | Orf38 HisTag C-Ter | 400 AU/mL |

13. Antimicrobial Agar Diffusion Test

The antibacterial activity was assessed against a set of Gram-negative and Gram-positive bacteria (Table 1), with the agar diffusion test. The cell free supernatant (CFS) used for antibacterial activity was obtained by centrifugation of an overnight culture of *Lactobacillus paracasei* CNCM I-5369 (8000 g, 10 min, 4° C.), grown at 37° C. for 18-24 h on MRS broth. After inoculation the indicator strain at 1% (v/v) in melted soft 1% BHI agar at 42° C., the medium was poured into Petri plates and left for 20 min under laminar hood. Then wells were made in the solidified BHI soft agar and 50 µl of CFS or E20 fraction adjusted to pH4.5-5, were poured into the wells. The Petri plates were left at room temperature, in sterile conditions, for 1 h before their incubation for 18 h at an adequate temperature. After this period, the antibacterial activity was detected by measuring the inhibition zones around the well containing the CFS or E20 fractions.

Table 13 shows the antimicrobial activity of cell-free supernatant (CFS) from *Lb. paracasei* I-CNCM 596 and E20 fractions

TABLE 13

| Strain | CFS | E20 |
|---|---|---|
| *Escherichia coli* ATCC8739 | + | ++ |
| *E. coli* ATCC25922 | + | ++ |
| *E. coli* 184 | + | ++ |

TABLE 13-continued

| Strain | CFS | E20 |
|---|---|---|
| *Acinetobacter baumanii* 9011 | ± | ± |
| *Bacillus cereus* (ICV* Lab collection) | – | – |
| *Citrobacter freundii* 11042 | ± | + |
| *Enterococcus faecalis* JH2.2 | – | – |
| *Listeria innocua* CIP80.01 | + | ++ |
| *Listeria monocytogenes* 162 | ± | + |
| *Klebsiella pneumoniae* 11016 | + | ++ |
| *Kocuria rhizophila* CIP 53.45 | + | ++ |
| *Proteus mirabilis* 11060 | ± | + |
| *Proteus vulgaris* (ICV Lab collection) | + | + |
| *Pseudomonas aeruginosa* ATCC27583 | ± | ± |
| *Pseudomonas aeruginosa* (ICV Lab collection) | ± | + |
| *Salmonella enterica* Newport (ICV Lab collection) | ± | + |
| *Staphylococcus epidermidis* (ICV Lab collection) | + | + |
| *Staphylococcus aureus* SA1 MRSA (ICV Lab collection) | + | + |
| *S. aureus* ATCC 44300 MRSA | + | + |

Width of inhibition zone "–": no activity; ±: 0 to 1 mm; +: 1 to 3 mm; ++: 3 to 6 mm".
*ICV: Institut Charles Viollette, Université de Lille, France As shown on Table 13, most of the Gram-negative and Gram-positive bacteria were affected by the E20 fraction as marked by clear inhibition zones. The CFS was less active, however *Escherichia coli, Staphylococcus aureus* and *Listeria* strains tested were clearly inhibited with inhibition zones of 1 to 3 mm.

14. Quantification of Antimicrobial Activities of Recombinant Peptides

The antimicrobial activity of the purified recombinant peptides was determined and expressed in arbitrary units per milliliters (AU/mL). The mix of the recombinant peptides was obtained by adding equal volume (100 µl) of each peptide and vortexing. Briefly the active samples were serially diluted in an ultrapure water, and their pH were adjusted to pH 4.5-5 using acetic acid, according to the following dilution ratio: 1/2, 1/4, 1/8, 1/16, 1/32 and 1/64. Afterwards, 10 µL of each diluted supernatant were deposited on 1% BHI medium-agar previously inoculated with *E. coli* 184, used as the indicator strain (mcr-1$^+$). The plates were incubated at 4° C. for 1 h and then at 37° C. for 18 h. The antibacterial activity expressed in AU/mL, is defined as the reciprocal of the highest dilution ($2^n$) that results in the inhibition of the indicator strain. The AU/mL is defined as $2^n \times 100$ µL/volume deposited (µL).

Table 14 shows the Antimicrobial activity of the fusion recombinant peptides against *E. coli* 184.

TABLE 14

| Recombinant peptide (C-terminal His-Tag) | Antimicrobial activity AU/mL |
|---|---|
| ORF010 | 200 |
| ORF012 | 200 |
| ORF023 | 200 |
| ORF030 | 200 |
| ORF038 | 400 |
| Mix of all recombinant peptides | 800 |

Each purified recombinant peptide has shown antimicrobial activity ranging from 200 to 400 AU/ml, while that registered for the mix of the five recombinant peptides was of 800 AU/ml.

15. Resistance of *L. paracasei* CNCM I-5369 to Conditions of the Simulated Gastrointestinal Conditions in Piglet A static in vitro digestion model of piglet was used to assess the viability of *L. paracasei* CNCM I-5369 to such conditions.

Indeed, this model reproduces parameters such as temperature, pH, bile salts concentration and enzymes involved in the digestion process of the piglet gastrointestinal (GI) environment. Of note, the effect of pH variation alone was studied in parallel, as well. Mouth, stomach and small intestine steps of digestion were simulated using fluids mimicking physiological conditions of each step and compartment. After 18 to 24 h of culture in MRS medium at 37° C., *Lactobacillus* cells were collected by centrifugation (8,000 g, 4° C., 10 min). The cell-pellets were washed twice in the adequate volume of PBS buffer. Mouth step reproduced buccal conditions with a pH adjusted 6.8 to 7 under agitation at 140 rpm, 39° C. for 5 min. Afterwards, the gastric step was simulated by addition of gastric fluid containing 15 U/mL of porcine pepsin (Sigma Aldrich) (pH 3-3.5). This step of 30 min was conducted in similar conditions of temperature and agitation as the previous step (39° C. at 140 rpm). Then, 1M NaOH solution was added to the batch in order to rise the pH solution up to pH 6, stopping pepsin digestion and mimicking the passage from the stomach to the duodenum compartment. The duodenum phase included addition of pancreatic enzymes (Trypsine 40 U/µL; Chymotrypsine 5 U/mL) (Sigma Aldrich) and bile (60 g/L) (Sigma Aldrich). Then the intestinal digestion process was carried out over 2 h, at pH 6 (39° C. at 140 rpm). After each step of this simulated digestion process, samples of *Lactobacillus* cells were collected and diluted in a saline buffer. Then 100 µL of adequate dilutions were plated on MRS agar plates and incubated at 37° C. for 18 to 24 h to allow sufficient growth. The number of colonies forming unit (CFU) per millilitre were determined. Statistical analysis. Data were expressed as a mean±standard error calculated over three independent experiments. Analysis of statistical significance was done using oneway ANOVA and the post-hoc Tukey Test (P<0.05) using XL-STAT (Addinsoft, Bordeaux, France).

Figure 13:
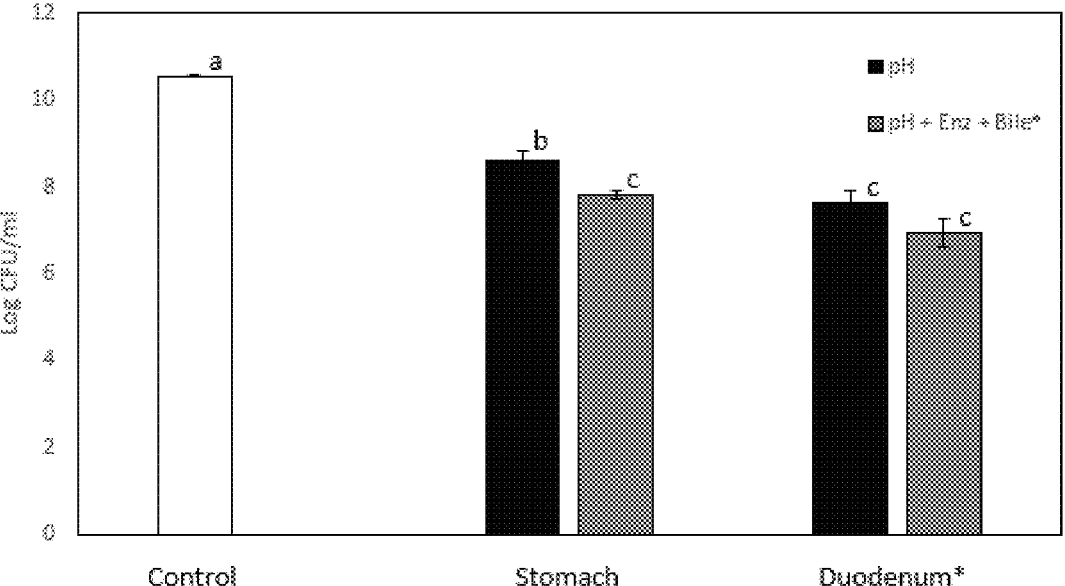
FIG. 13 shows the number of *L. paracasei* CNCM I-5369 cells in different compartments of the static process of piglet in vitro model of digestion: in the mouth (initial inoculum/control), stomach and duodenum, due to the effect of pH variation (black bars) in each compartment or to the effect of pH variation combined to enzymes and bile (bile was added in the simulated duodenum compartment) (dark grey bars)

The obtained results are shown in FIG. 13, which illustrates the number of *L. paracasei* CNCM I-5369 cells in different compartments of the static process of piglet in vitro model of digestion: in the mouth (initial inoculum/control), stomach and duodenum, due to the effect of pH variation (black bars) in each compartment or to the effect of pH variation combined to enzymes and bile (bile was added in the simulated duodenum compartment) (dark grey bars). Samples were taken at each step of digestion and the number of CFU/mL was determined on the agar medium. Data were expressed in percentage of the total yeast cells poured on a Caco-2 confluent monolayer. Values±SD are means of triplicates. Statistical analysis was made using XL-STAT software. Columns with different letters are significantly different (P<0.05) using one-way ANOVA with Tukey post-hoc analysis.

Collectively these data show that *Lactobacillus paracasei* CNCM I-5369 has a good resistance to the conditions occurring during the simulated digestion process in piglet. The initial number of living bacterial cells, of ~$10^{10}$ CFU/mL at the beginning of the digestion process has decreased by 2 to 3 logs. This decrease is very likely attributable to the pH variation. This was noteworthy in the stomach compartment.

16. Cytotoxicity Assay

Safety of *Lactobacillus paracasei* CNCM I-5369 and that of E20 fraction were assessed in vitro using crystal violet (Sigma Aldrich) staining assay, on Caco-2 cells human colorectal adenocarcinoma cells. Caco-2 cells were seeded at a density of $6\times10^4$ cells/well in 96-well cell culture plates and pre-incubated for 7 days. The overnight *Lactobacillus* culture and E20 fraction were prepared in PBS and then applied onto confluent Caco-2 cell monolayers at a ratio of MOI (Multiplicity of infection) 1:10 and 1:100 for Caco-2/*Lactobacillus* and diluted E20 fraction 4X and 8X (X=fold). After incubation, the medium was removed and cells were washed 2× with PBS and incubated with 150 µL of crystal violet dye at 0.5% (w/v) and incubated 20 min at room temperature with shaking. After removing the dye and washing with deionized water, the plate was dried, and the remaining dye was solubilized by adding 200 µL of methanol in the wells. The relative viability (%) was then calculated based on absorbance at 570 nm using microplate reader (Xenius SAFAS, Monaco, France). Results were expressed as percentage of proliferation compared to the viability of untreated control cells. Triton X100 detergent (Sigma Aldrich) was used as positive control of cytotoxicity at 0.01% (v/v).

Figure 14:
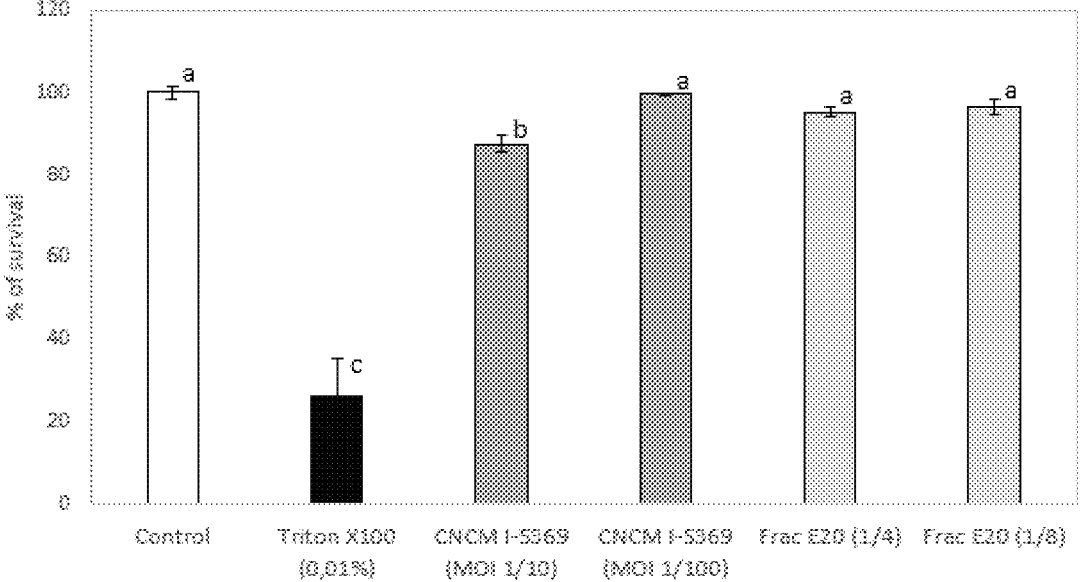
FIG. 14 shows the survival percentages of Caco-2 following their treatment with several *Lactobacillus* strains for 24 h at a MOI of 1/10 or 1/100 (Caco2/*Lactobacillus*) cells ratio and with diluted E20 fraction.

The results are shown in FIG. 14, which illustrates the survival percentages of Caco-2 following their treatment with several *Lactobacillus* strains for 24 h at a MOI of 1/10 or 1/100 (Caco2/*Lactobacillus*) cells ratio and with diluted E20 fraction. Triton X100 detergent at 0.01% was used as positive test under similar conditions. Values are means±SD of three independent measurements. Statistical analysis was made using XL-STAT software. Columns with different letters are significantly different (P<0.05) using one-way ANOVA with Tukey post-hoc analysis.

The data of FIG. 14 showed survival rates of Caco-2 >90%, supporting therefore the safety absence of cytotoxicity for *Lactobacillus paracasei* CNCM I-5369 at both MOI tested and as well for diluted E20 fraction. Of note, similar results were obtained with intestinal porcine epithelial IPEC-1 cells.

17. Inhibition of *E. coli* 184 Adhesion to Caco-2 and IPEC-1 Cells by *Lactobacillus* Strains Human colorectal adenocarcinoma Caco-2 cells and intestinal porcine epithelial IPEC-1 cells were used in order to establish the adhesion and inhibition assays. With regard to that, cells were grown at 37° C. in presence of 5% (v/v) $CO_2$ in Dulbecco's Modified Eagle Medium (DMEM) containing 4.5 g/L of glucose and supplemented with L-glutamine (2 mM), penicillin (100 U/mL), streptomycin (100 µg/mL), 10% of heat-inactivated fetal bovine serum (FBS) and 1% (v/v) non-essential amino acids. Then 24-wells tissue culture plates were used to prepare monolayers of Caco-2 and IPEC-1 cells. Wells were inoculated with $4\cdot10^4$ Caco-2/IPEC-1 cells per well, and the plates were incubated for 7 days. Two different protocols were used to discriminate competition/exclusion of *E. coli* 184 by bacteriocins producing strain *Lactobacillus paracasei* CNCM I-5369, and non-producing bacteriocin *Lactobacillus paracasei* FB1.

For exclusion tests, *Lactobacillus* strains (~$10^8$ CFU/mL) were washed with 1 mL of PBS and resuspended in DMEM serum and antibiotic free. Then, they were added to Caco-2/IPEC-1 cell monolayers and incubated for 90 min at 37° C. (5% $CO_2$). Afterwards, non-adherent *Lactobacillus* strains were removed by washing twice with PBS, and *E. coli* 184 (~$10^7$ CFU/mL), prepared in the same way as *Lactobacillus* strain. They were added and incubated for additional 2 h at 37° C.

For competition tests, *Lactobacillus* ($10^8$ CFU/mL) and pathogen ($10^7$ CFU/mL) strains prepared as above-indicated were mixed and added to Caco-2/IPEC-1 monolayers and incubated for 2 h at 37° C. Caco-2/IPEC-1 monolayers were washed 2× with 500 µL of PBS and incubated with 200 µL of Trypsin/EDTA for 15 min to remove Caco-2/IPEC-1 cells with adherent bacteria.

After exclusion and competition tests, the number of adherents, *E. coli* 184 cells was performed on Eosine Methylene Blue (EMB). The pathogen adhesion rates were determined, in comparison to the control (well containing pathogens without *Lactobacillus* strains) which represents 100% adhesion. The obtained results are shown in FIGS. 15A and 15B, which illustrate the percentages of adhesion of *E. coli* 184 strain to: Caco-2 monolayer cells in FIG. 15A; IPEC-1 monolayer cells in FIG. 15B; (white) alone, or during competition and exclusion assays in presence of (black) *Lactobacillus paracasei* CNCM I-5369 (bac+) strain, or in presence of (grey) of *Lactobacillus paracasei* FB1 (bac−) strain. Values are means±SD of three independent measurements. Statistical analysis was made using XL-STAT software. Columns with different letters are significantly different (P<0.05) using one-way ANOVA with Tukey post-hoc analysis.

As shown in FIGS. 15A-B, it is clear that the bacteriocins-producing *Lactobacillus paracasei* CNCM I-5369 (bac+) reduced the number of adherent *E. coli* 184, on Caco-2 and IPEC-1 monolayers, by 80 to 90% compared to the control assay (without treatment). Of note, the non-producing bacteriocin *Lactobacillus paracasei* FB1 (bac−) strain did not impact the adhesion of *E. coli* 184 to piglet IPEC-1 monolayer. However, this strain was able to reduce the number of adherent *E. coli* on human Caco-2 monolayer cells of ~60-70% compared to the untreated control. This remains significantly below that obtained for *Lactobacillus paracasei* CNCM I-5369.

18. DPPH Radical Scavenging Activity of Intact Cells and Intracellular Cell-Free Extracts Lactobacilli cells were grown in MRS medium for 18 h at 37° C., and cells were harvested by centrifugation (8000 g at 4° C. for 10 min). Cells were washed 3× with PBS (10 mM, pH 7.2) and resuspended in PBS, at $1^{10}$ CFU/mL, enabling to obtain intact cells. Moreover, to prepare intracellular cell-free extracts, cell-pellets were quickly washed 2× with a deionized water and resuspended at $1^{10}$ CFU/mL in the same solution before to be transferred to NucleoSpin® Bead Tubes Type B (Macherey-Nagel). Tubes were homogenized for 3 cycles of 30 s each, using the FastPrep-24 5G (MP Biomedicals) with cooling on ice bath for 5 min between each cycle. Cell debris was removed by centrifugation (8000 g, 4° C., 10 min), and the resulting supernatant corresponds to the intracellular cell-free extract. The scavenging of DPPH was analyzed using 0.8 ml of intact cells and intracellular cell-free extract mixed with 1 mL of freshly prepared DPPH solution (0.004%, w/v in methanol), and incubated for 30 min in dark conditions. Blank samples contained either PBS or deionized water. The scavenged DPPH was then monitored by measuring the decrease in absorbance at 515 nm. The scavenging ability was defined as the following formula and reported in the Table 15:

$$\% \text{ of scavenging} = [1 - A_{515}(\text{sample})/A_{515}(\text{blank})]\ 100\%.$$

These results show that *Lactobacillus paracasei* CNCM I-5369 has an antioxidant effect.

19. In Vitro Cholesterol Lowering

The cholesterol reduction in vitro by *Lactobacillus para-casei* CNCM I-5369 was investigated by measuring the residual cholesterol in MRS broth supplemented with 0.3% (w/v) bile salts. Briefly, 10 mg of pure cholesterol were dissolved in 500 μL of ethanol (Sigma-Aldrich), and added to 100 mL of MRS broth supplemented with 0.3% (w/v) of porcine bile (Sigma-Aldrich). The medium was inoculated with *Lactobacillus* strain and incubated for 24 h at 37° C. (test medium). After this period of incubation, cells were harvested by centrifugation (8,000 g, 4° C., 10 min), and the cell-free supernatant was used for cholesterol quantification. Non-inoculated broth was considered as control (control medium). To 1 mL culture supernatant, 3 mL of 95% (v/v) ethanol were added, followed by 2 mL of 50% (w/v) potassium hydroxide (KOH, Sigma Aldrich), and the contents were mixed after addition of each component. The tubes were heated for 10 min at 60° C. After cooling, 5 mL of hexane (Sigma-Aldrich) were dispensed into all tubes and vortexed for 5 min, and then 3 mL of water were added and mixed thoroughly. Tubes were allowed to stand for 20 min at 30° C. to allow phase separation. A volume of 2.5 mL of hexane layer was then transferred to a fresh tube and allowed to dry completely; 1.5 mL ferric chloride reagent (Sigma-Aldrich) were added and the tube allowed standing for 10 min. One mL of concentrated sulfuric acid (Sigma-Aldrich) was added from the sides of the test tubes. The mixture was vortexed and allowed to stand for 45 min at 30° C. The absorbance was measured at 540 nm. The cholesterol standard graph was established using pure cholesterol (Sigma-Aldrich) and used to determine cholesterol concentration. The percentage of assimilation was then calculated using the following formula:

$$Assimilation\,(\%) = \cfrac{\left(\cfrac{[\text{cholesterol in control medium}]-}{[\text{cholesterol in test medium}]}\right)\times 100}{[Conc.\ \text{cholesterol in control medium}]}$$

The results were reported in Table 15.

TABLE 15

| | Scavenging activity | | *r*Cholesterol assimilation % MRS broth (0.1 mg/ml cholesterol and 0.3% bile salts) |
|---|---|---|---|
| | Intact cells | Intracellular extract | |
| *Lactobacillus paracasei* CNCM I-5369 (bac+) | 32% | 15% | 74.8% |

As shown in Table 15, it appears that the DPPH scavenging activity and cholesterol assimilation of intact *Lactobacillus paracasei* CNCM I-5369 reached interesting rates of 32 and 78% respectively.

The invention claimed is:

1. A pharmaceutical composition comprising: (1) a peptide selected from SEQ ID NO:1 to SEQ ID NO:5, or a combination thereof; (2) a *Lactobacillus paracasei* strain ICVB411 deposited under number CNCM I-5369; (3) sodium alginate nanoparticles; and (4) a pharmaceutically acceptable excipient.

2. The pharmaceutical composition of claim 1, further comprising at least one of: colistin, essential oil of mint, essential oil of thyme, essential oil of pine tree, menthol, thymol, pinene, vitamin C, formic acid, propionic acid, citric acid, sorbic acid, and lactic acid.

3. The pharmaceutical composition of claim 1, having a pH between 4 and 5.

4. The pharmaceutical composition of claim 1, said sodium alginate nanoparticles have an average size between 115 nm and 126 nm.

5. The pharmaceutical composition of claim 1, wherein said sodium alginate nanoparticles are loaded with a mixture comprising: the peptide selected from SEQ ID NO:1 to SEQ ID NO:5 or a combination thereof; and at least one component selected from the group consisting of: essential oil of mint, essential oil of thyme, essential oil of pine tree, menthol, thymol, pinene, vitamin C, formic acid, propionic acid, citric acid, sorbic acid, and lactic acid.

6. The pharmaceutical composition of claim 5, wherein said sodium alginate nanoparticles are further loaded with a supernatant of a culture of the *Lactobacillus paracasei* strain ICVB411.

7. The pharmaceutical composition of claim 1, wherein said sodium alginate nanoparticles are loaded with colistin and at least one component selected from the group consisting of: essential oil of mint, essential oil of thyme, essential oil of pine tree, menthol, thymol, pinene, vitamin C, formic acid, propionic acid, citric acid, sorbic acid, and lactic acid.

8. The pharmaceutical composition of claim 1, further comprising a supernatant of a culture of the *Lactobacillus paracasei* strain ICVB411, said supernatant being optionally purified.

9. The pharmaceutical composition of claim 1, wherein said sodium alginate nanoparticles are loaded with a mixture of the peptide selected from SEQ ID NO:1 to SEQ ID NO:5, or a combination thereof; and a supernatant of a culture of the *Lactobacillus paracasei* strain ICVB411.

\* \* \* \* \*